US006255336B1

(12) United States Patent
Shayman et al.

(10) Patent No.: US 6,255,336 B1
(45) Date of Patent: **\*Jul. 3, 2001**

(54) AMINO CERAMIDE-LIKE COMPOUNDS AND THERAPEUTIC METHODS OF USE

(75) Inventors: James A. Shayman, Ann Arbor, MI (US); Norman S. Radin, Menlo Park, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/350,768

(22) Filed: Jul. 9, 1999

Related U.S. Application Data

(60) Continuation-in-part of application No. 08/883,218, filed on Jun. 26, 1997, now Pat. No. 6,051,598, which is a division of application No. 08/708,574, filed on Sep. 5, 1996, now Pat. No. 5,916,911.
(60) Provisional application No. 60/004,047, filed on Sep. 20, 1995.

(51) Int. Cl.[7] .................. A61K 43/36; C07D 207/08; C07D 405/06

(52) U.S. Cl. .................. 514/422; 514/428; 548/526; 548/568

(58) Field of Search .................. 514/428, 422; 548/526, 568

(56) References Cited

U.S. PATENT DOCUMENTS

| 5,631,394 | 5/1997 | Wei et al. ........................ 556/404 |
| 6,030,995 | * 2/2000 | Shayman et al. .................. 514/428 |
| 6,051,598 | * 4/2000 | Shayman et al. .................. 514/428 |

OTHER PUBLICATIONS

Abe, A. et al., "Improved Inhibitors of Glucosylceramide Synthesis," *J. Biochem.* 111:191–196 (1992).
Abe, A. et al., "Metabolic Effects of Short–Chain Ceramide and Glucosylceramide on Sphingolipids and Protein Kinase C," *Eur. J. Biochem.* 210:765–773 (1992).
Abdel–Magid, A. et al., "Metal–Assisted Aldol Condensation of Chiral A–Halogenated Imide Enolates: A Stereocontrolled Chiral Epoxide Synthesis," *J. Am. Chem. Soc.* 108:4595–4602 (1986).
Alon, R. et al., "Glycolipid Ligands for Selectins Support Leukocyte Tethering & Rolling Under Physiologic Flow Conditions," *J. Immunol.*, 154:5356–5366 (1995).
Bielawska, A. et al., "Modulation of Cell Growth and Differentiation by Ceramide," *FEBS Letters* 307:211–214 (1992).
Bielawska, A. et al., "Ceramide–Mediated Biology. Determination of Structural and Stereospecific Requirements Through the Use of N–Acyl–Phenylaminoalcohol Analogs," *J. Biol. Chem.* 267:18493–18497 (1992).

Blobe, G.C. et al., "Regulation of PKC and Its Role in Cancer Biology," *Cancer Metastasis Rev.* 13:411–431 (1994).
Brenkert, A. et al., "Synthesis of Galactosyl Ceramide and Glucosyl Ceramide by Rat Brain: Assay Procedures and Changes with Age," *Brain Res.* 36:183–193 (1972).
Carson, K.G. et al., "Studies on Morpholinosphingolipids: Potent Inhibitors of Glucosylceramide Synthase," *Tetrahedron Lett.* 35:2659–2662 (1994).
Evans, D.A. et al., "Stereoselective Aldol Condensations Via Boron Enolates," *J. Am. Chem. Soc.* 103:3099–3111 (1981).
Felding–Habermann, B. et al., "A Ceramide Analog Inhibits T Cell Proliferative Response Through Inhibition of Glycosphingolipid Synthesis and Enhancement of N,N–Dimethylsphingosine Synthesis," *Biochemistry* 29:6314–6322 (1990).
Gatt, S. et al., "Assay of Enzymes of Lipid Metabolism With Colored and Fluorescent Derivatives of Natural Lipids," *Meth. Enzymol.* 72:351–375 (1981).
Hakomori, S. "New Directions in Cancer Therapy Based on Aberrant Expression of Glycosphingolipids: Anti–adhesion and Ortho–Signaling Therapy," *Cancer Cells* 3:461–470 (1991).
Hospattankar, A.V. et al., "Changes in Liver Lipids After Administration of 2–Decanoylamino–3–Morpholinopropiophenone and Chlorpromazine," *Lipids* 17:538–543 (1982).
Inokuchi, J. et al., "Preparation of the Active Isomer of 1–Phenyl–2–Decanoylamino–3–Morpholino–1–Propanol, Inhibitor of Glucocerebroside Synthetase," *J. Lipid Res.* 28:565–571 (1987).
Inokuchi, J. et al., "Antitumor Activity in Mice of an Inhibitor of Glycosphingolipid Biosynthesis," *Cancer Lett.* 38:23–30 (1987).
Inokuchi, J. et al., "Inhibition of Experimental Metastasis of Murine Lewis Long Carcinoma by an Inhibitor of Glucosylceramide Synthase and its Possible Mechanism of Action," *Cancer Res.* 50:6731–6737 (1990).
Jaffrezou,J. et al., "Inhibition of Lysosomal Acid Sphingomyelinase by Agents which Reverse Multidrug Resistance," *Biochem. Biophys. Acta* 1266:1–8 (1995).
Kalën, A. et al., "Elevated Ceramide Levels in GH4C1 Cells Treated with Retinoic Acid," *Biochim. Biophys. Acta* 1125:90–96 (1992).
Kopaczyk, K. C. et al., "In Vivo Conversions of Cerebroside and Ceramide in Rat Brain," *J. Lipid Res.* 6:140–145 (1965).

(List continued on next page.)

Primary Examiner—Richard L. Raymond
(74) Attorney, Agent, or Firm—Harness, Dickey & Pierce, P.L.C.

(57) ABSTRACT

Novel amino ceramide-like compounds are provided which inhibit glucosyl ceramide (GlcCer) formation by inhibiting the enzyme GlcCer synthase, thereby lowering the level of glycosphingolipids. The compounds of the present invention have improved GlcCer synthase inhibition activity and are therefore highly useful in therapeutic methods for treating various conditions and diseases associated with altered glycosphingolipid levels.

11 Claims, 12 Drawing Sheets

OTHER PUBLICATIONS

Nakamura, K. et al., "Coomassie Brilliant Blue Staining of Lipids on Thin–Layer Plates," *Anal. Biochem.* 142:406–41 (1984).

Nicolau, K.C. et al., "A Practical and Enantioselective Synthesis of Glycosphingolipids and Related Compounds. Total Synthesis of Globotriaosylceramide ($Gb_3$)," *J. Am. Chem. Soc.* 110:7910–7912 (1988).

Preiss, J.E. et al., "Quantitative Measurement of SN–1, 2–Diacylglycerols Present in Platelets, Hepatocytes, and Ras– and Sis–Transformed Normal Rat Kidney Cells," *J. Biol. Chem.* 261:8597–8600 (1986).

Radin, N.S. et al., "Use of 1–Phenyl–2–Decanoylamino–3–Morpholino–1–Propanol (PDMP), an Inhibitor of Glucosylceramide Synthesis," In *NeuroProtocols, A Companion to Methods in Neurosciences,* S. K. Fisher et al., Ed., (Academic Press, San Diego) 3:145–155 (1993).

Radin, N.S. et al., "Metabolic Effects of Inhibiting Glucosylceramide Synthesis with PDMP and Other Substances," In *Advances in Lipid Research; Sphingolipids in Signaling, Part B.,* R.M. Bell et al., Ed. (Academic Press, San Diego) 28:183–213 (1993).

Radin N.S. et al., "Ultrasonic Baths as Substitutes for Shaking Incubator Baths," *Enzyme* 45:67–70 (1991).

Rosenwald, A.G. et al., "Effects of the Glycosphingolipid Synthesis Inhibitor, PDMP, on Lysosomes in Cultured Cells," *J. Lipid Res.* 35:1232 (1994).

Rosenwald, A.G. et al., "Effects of a Sphingolipid Synthesis Inhibitor on Membrane Transport Through the Secretory Pathway," *Biochemistry* 31:3581–3590 (1992).

Shayman, J.A. et al., "Modulation of Renal Epithelial Cell Growth by Glucosylceramide: Association with Protein Kinase C, Sphingosine, and Diacylglyceride," *J. Biol. Chem.* 266:22968–22974 (1991).

Shukla, G.S. et al., "Glucosylceramide Synthase of Mouse Kidney: Further Characterization and Improved Assay Method," *Arch. Biochem. Biophys.* 283:372–378 (1990).

Shukla, A. et al., "Metabolism of D–[$^3$H]PDMP, an Inhibitor of Glucosylceramide Synthesis, and the Synergistic Action of an Inhibitor of Microsomal Monooxygenase," *J. Lipid Res.* 32:713–722 (1991).

Skehan, P. et al., "New Colorimetric Cytotoxicity Assay for Anticancer–Drug Screening," *J. Natl. Cancer Inst.* 82:1107–1112 (1990).

Strum, J.C. et al., "1–β–D–Arabinofuranosylcytosine Stimulates Ceramide and Diglyceride Formation in HL–60 Cells," *J. Biol. Chem.* 269:15493–15497 (1994).

Svensson, M. et al., "Epithelial Glucosphingolipid Expression as a Determinant of Bacterial Adherence and Cytokine Production," *Infect. and Immun.* 62:4404–4410 (1994).

Tang, W. et al., "Phorbol Ester Inhibits 13–Cis–Retinoic Acid–Induced Hydrolysis of Phosphatidylinositol 4,5–Biphosphate in Cultured Murine Keratinocytes: a Possible Negative Feedback Via Protein Kinase C–Activation," *Cell Bioch. Funct.* 9:183–191 (1991).

Uemura, K. et al., "Effect of an Inhibitor of Glucosylceramide Synthesis on Cultured Rabbit Skin Fibroblasts," *J. Biochem.* (*Tokyo*) 108:525–530 (1990).

Vunnam, R.R. et al., "Analogs of Ceramide that Inhibit Glucocerebroside Synthetase in Mouse Brain," *Chem. Phys. Lipids* 26:265–278 (1980).

Zador, I.Z. et al., "A Role for Glycosphingolipid Accumulation in the Ranal Hypertrophy of Streptozotocin–Induced Diabetes Mellitus," *J. Clin. Invest.* 91:979–803 (1993).

Ziche, M. et al., "Angiogenesis Can Be Stimulated or Repressed in In Vivo by a Change in GM3:GD3 Ganglioside Ratio," *Lab. Invest.* 67:711–715 (1992).

Abe, A. et al., "Structural and stereochemical studies of potent inhibitors of glucosylceramide synthase and tumor cell growth," *J. Lipid Res.* 36:611–621 (1995).

Abe, A. et al., "Induction of glucosylceramide synthase by synthase inhibitors and ceramide," *Biochim. Biophys. Acta* 1299:331–341 (1996).

Abe, A. et al., "Metabolic Effects of Short–Chain Ceramide and Glucosylceramide on Sphingolipids and Protein Kinase C," *Eur. J. Biochem.* 210:765–773 (1992).

Ames, B.N., "Assay of Inorganic Phosphate, Total Phosphate and Phosphatases," *Methods Enzymol.* 8:115–118 (1966).

Högberg, T. et al., Theoretical and experimental methods in drug design applied on antipsychotic dopamine antagonists. Larsen, P.K., and Bundgaard, H., "Textbook of Drug Design and Development," pp. 55–91 (1991).

Shayman, J.A. et al., "Glucosphingolipid Dependence of Hormone–stimulated Inositol Triphoshpate Formation," *J. Biol. Chem.* 265:12135–12138 (1990).

Skukla, G. et al., "Rapid kidney changes resulting from glycosphingolipid depletion by treatment with a glucosyltransferase inhibitor," *Biochim. Biophys. Acta* 1083:101–108 (1991).

Abe, A. et al., "Structural and stereochemical studies of potent inhibitors of glucosylceramide synthase and tumor cell growth." *Chemical Abstracts* 122(23):281432s pp. 32 (1995).

* cited by examiner

R=

D-*threo*-1-phenyl-2-palmitoylamino-3-pyrrolidino-1-propanol (P4)

D-*threo*-1-(3',4'-ethylenedioxy)phenyl-2-palmitoylamino-3-pyrrolidino-1-propanol D-*threo*-1-(3',4'-trimethylenedioxy)phenyl-2-palmitoylamino-3-pyrrolidino-1-propanol D-*threo*-1-(3',4'-methylenedioxy)phenyl-2-palmitoylamino-3-pyrrolidino-1-propanol D-*threo*-4'-hydroxy-1-phenyl-2-palmitoylamino-3-pyrrolidino-1-propanol (P4)

AMINO CERAMIDE-LIKE COMPOUNDS AND THERAPEUTIC METHODS OF USE

RELATED APPLICATIONS

The present application is a continuation-in-part of U.S. Ser. No. 08/883,218, filed Jun. 26, 1997, now U.S. Pat. No. 6,051,598, which is a divisional of U.S. Ser. No. 08/708,574, filed Sep. 5, 1996, now U.S. Pat. No. 5,916,911, which claims priority from U.S. Ser. No. 60/004,047, filed Sep. 20, 1995, all of which are hereby expressly incorporated by reference.

SPONSORSHIP

The present invention was supported by grant nos. R01 DK41487, R01 DK69255 and RO139255 from the National Institutes of Health, contract R43 CA 58159 from the National Cancer Institute, grant GM 35712 from the National Institute of General Medical Sciences, and by the University of Michigan Comprehensive Cancer Center grant 2P30 CA 46592 from the National Cancer Institute, U.S. Public Health Service, DHHS. Grant number for Merit Award from Veteran's Administration? The government may have certain rights in this invention.

FIELD OF THE INVENTION

The present invention relates generally to ceramide-like compounds and, more particularly, to ceramide-like compounds containing a tertiary amine group and their use in therapeutic methods.

BACKGROUND OF THE INVENTION

Hundreds of glycosphingolipids (GSLs) are derived from glucosylceramide (GlcCer), which is enzymatically formed from ceramide and UDP-glucose. The enzyme involved in GlcCer formation is UDP-glucose:N-acylsphingosine glucosyltransferase (GlcCer synthase). The rate of GlcCer formation under physiological conditions may depend on the tissue level of UDP-glucose, which in turn depends on the level of glucose in a particular tissue (Zador, I. Z. et al., "A Role for Glycosphingolipid Accumulation in the Renal Hypertrophy of Streptozotocin-Induced Diabetes Mellitus," *J. Clin. Invest.* 91:797–803 (1993)). In vitro assays based on endogenous ceramide yield lower synthetic rates than mixtures containing added ceramide, suggesting that tissue levels of ceramide are also normally rate-limiting (Brenkert, A. et al., "Synthesis of Galactosyl Ceramide and Glucosyl Ceramide by Rat Brain: Assay Procedures and Changes with Age,+ *Brain Res.* 36:183–193 (1972)).

It has been found that the level of GSLs controls a variety of cell functions, such as growth, differentiation, adhesion between cells or between cells and matrix proteins, binding of microorganisms and viruses to cells, and metastasis of tumor cells. In addition, the GlcCer precursor, ceramide, may cause differentiation or inhibition of cell growth (Bielawska, A. et al., "Modulation of Cell Growth and Differentiation by Ceramide," *FEBS Letters* 307:211–214 (1992)) and be involved in the functioning of vitamin $D_3$, tumor necrosis factor-$\alpha$, interleukins, and apoptosis (programmed cell death). The sphingols (sphingoid bases), precursors of ceramide, and products of ceramide catabolism, have also been shown to influence many cell systems, possibly by inhibiting protein kinase C (PKC).

It is likely that all the GSLs undergo catabolic hydrolysis, so any blockage in the GlcCer synthase should ultimately lead to depletion of the GSLs and profound changes in the functioning of a cell or organism. An inhibitor of GlcCer synthase, PDMP (1R-phenyl-2R-decanoylamino-3-morpholino-1-propanol), previously identified as the D-threo isomer (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987)), has been found to produce a variety of chemical and physiological changes in cells and animals (Radin, N. S. et al., "Use of 1-Phenyl-2-Decanoylamino-3-Morpholino-1-Propanol (PDMP), an Inhibitor of Glucosylceramide Synthesis," In *NeuroProtocols, A Companion to Methods in Neurosciences,* S. K. Fisher et al., Ed., (Academic Press, San Diego) 3:145–155 (1993) and Radin, N. S. et al., "Metabolic Effects of Inhibiting Glucosylceramide Synthesis with PDMP and Other Substances," In *Advances in Lipid Research; Sphingolipids in Signaling,* Part B., R. M. Bell et al., Ed. (Academic Press, San Diego) 28:183–213 (1993)). Particularly interesting is the compound's ability to cure mice of cancer induced by Ehrlich as cites carcinoma cells (Inokuchi, J. et al., "Antitumor Activity in Mice of an Inhibitor of Glycosphingolipid Biosynthesis," *Cancer Lett.* 38:23–30 (1987)), to produce accumulation of sphingosine and N,N-dimethylsphingosine (Felding-Habermann, B. et al., "A Ceramide Analog Inhibits T Cell Proliferative Response Through Inhibition of Glycosphingolipid Synthesis and Enhancement of N,N-Dimethylsphingosine Synthesis," *Biochemistry* 29:6314–6322 (1990)), and to slow cell growth (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). Compounds with longer chain fatty acyl groups have been found to be substantially more effective (Abe, A. et al., "Improved Inhibitors of Glucosylceramide Synthesis," *J. Biochem.* 111:191–196 (1992)).

The importance of GSL metabolism is underscored by the seriousness of disorders resulting from defects in GSL metabolizing enzymes. For example, Tay-Sachs, Gaucher's, and Fabry's diseases, resulting from enzymatic defects in the GSL degradative pathway and the accumulation of GSL in the patient, all have severe clinical manifestations. Another example of the importance of GSL function is seen in a mechanism by which blood cells, whose surfaces contain selecting, can, under certain conditions, bind to GSLs in the blood vessel walls and produce acute, life-threatening inflammation (Alon, R. et al., "Glycolipid Ligands for Selections Support Leukocyte Tethering & Rolling Under Physiologic Flow Conditions." *J. Immunol.,* 154:5356–5366 (1995)).

At present there is only one treatment available for patients with Gaucher disease, wherein the normal enzyme which has been isolated from normal human tissues or cultured cells is administered to the patient. As with any drug isolated from human material, great care is needed to prevent contamination with a virus or other dangerous substances. Treatment for an individual patient is extremely expensive, costing hundreds of thousands, or even millions of dollars, over a patient's lifetime. It would thus be desirable to provide a treatment which includes administration of a compound that is readily available and/or producible from common materials by simple reactions.

Possibly of even greater clinical relevance is the role of glucolipids in cancer. For example, it has been found that certain GSLs occur only in tumors; certain GSLs occur at abnormally high concentrations in tumors; certain GSLs, added to tumor cells in culture media, exert marked stimulatory or inhibitory actions on tumor growth; antibodies to certain GSLs inhibit the growth of tumors; the GSLs that are shed by tumors into the surrounding extracellular fluid inhibit the body's normal immunodefense system; the composition of a tumor's GSLs changes as the tumors become increasingly malignant; and, in certain kinds of cancer, the level of a GSL circulating in the blood gives useful information regarding the patient's response to treatment. Because of the significant impact GSLs have on several biochemical processes, there remains a need for compounds having improved GlcCer synthase inhibition activity.

It would thus be desirable to provide compounds which inhibit GlcCer synthase activity. It would also be desirable to provide compounds which inhibit GlcCer synthase activity, thereby lowering the level of GSLs and increasing GSL precursor levels, e.g. increasing the levels of ceramide and sphingols. It would further be desirable to provide compounds which inhibit GlcCer synthase activity and lower the level of GSLs without also increasing ceramide levels. It would also be desirable to provide compounds and therapeutic methods to treat conditions and diseases associated with altered GSL levels and/or GSL precursor levels.

SUMMARY OF THE INVENTION

Novel compounds are provided which inhibit GlcCer formation by inhibiting the enzyme GlcCer synthase, thereby lowering the level of GSLs. The compounds of the present invention have improved GlcCer synthase inhibition activity and are therefore highly useful in therapeutic methods for treating various conditions and diseases associated with altered GSL levels, as well as GSL precursor levels. For example, the compounds of the present invention may be useful in methods involving cancer growth and metastasis, the growth of normal tissues, the ability of pathogenic microorganisms to bind to normal cells, the binding between similar cells, the binding of toxins to human cells, and the ability of cancer cells to block the normal process of immunological cytotoxic attack.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
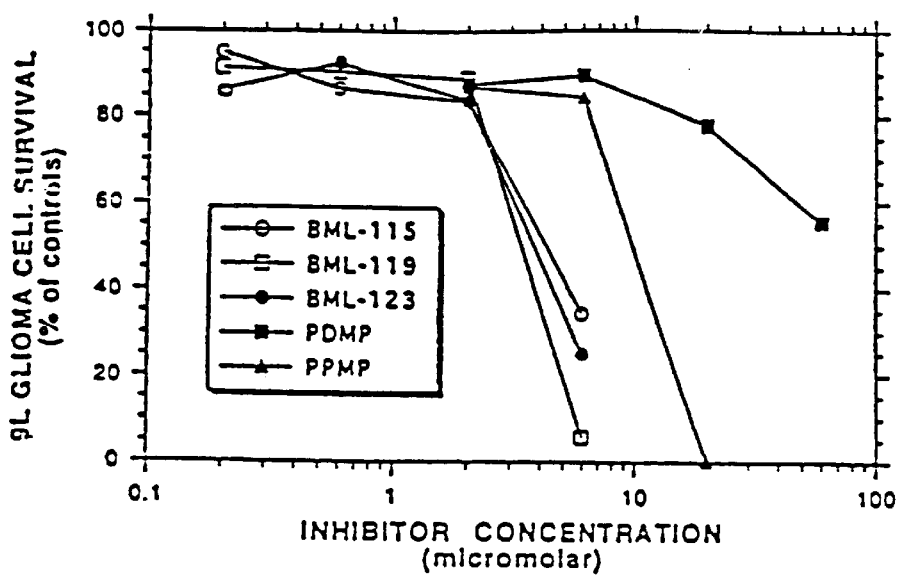
FIG. 1 is a graph showing the growth and survival of 9L gliosarcoma cells grown in medium containing different GlcCer synthase inhibitors.

Novel compounds are provided which inhibit GlcCer formation by inhibiting the enzyme GlcCer synthase, thereby lowering the level of GSLs. The compounds of the present invention have improved GlcCer synthase inhibitory activity and are therefore highly useful in therapeutic methods for treating various conditions and diseases associated with altered GSL levels.

The compounds of the present invention generally have the following formula:

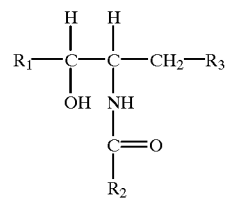

wherein $R_1$ is a phenyl group, preferably a substituted phenyl group such as p-methoxy, hydroxy, dioxane substitutions such as methylenedioxy, ethylenedioxy, and trimethylenedioxy, cyclohexyl or other acyclic group, t-butyl or other branched aliphatic group, or a long alkyl or alkenyl chain, preferably 7 to 15 carbons long with a double bond next to the kernel of the structure. The aliphatic chain can have a hydroxyl group near the two asymmetric centers, corresponding to phytosphingosine.

$R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the nitrogen atom is attached to the kernel (i.e., a tertiary amine).

All four structural isomers of the compounds are contemplated within the present invention and may be used either singly or in combination (i.e., DL-threo or DL-erythro).

The preferred aliphatic compound of the present invention is D-threo-1-pyrrolidino-1-deoxyceramide, identified as IV-231B herein and also referred to as PD. The preferred aromatic compound of the present invention is 1-phenyl-2-palmitoylamino-3-pyrrolidino-1-propanol, identified as BML-119 herein and also referred to as P4. The structures of the preferred compounds are as follows:

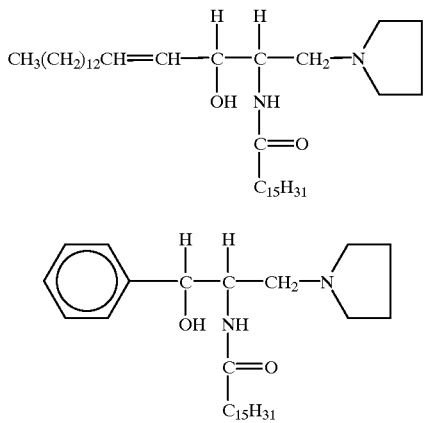

An additional preferred compound of the present invention are D-t-3',4'-ethylenedioxy-1-phenyl-2-palmitoylamino-3-pyrrolidino-1-propanol, also referred to herein as D-t-3',4'-ethylenedioxy-P4, and D-t-4'-hydroxy-1-phenyl-2-palmitoylamino-3-pyrrolidino-1-propanol, also referred to herein as D-t-4'-hydroxy-P4.

By increasing the acyl chain length of PDMP from 10 to 16 carbon atoms, the efficacy of the compounds of the present invention as GlcCer synthase inhibitors is greatly enhanced. The use of a less polar cyclic amine, especially a pyrrolidine instead of a morpholine ring, also increases the efficacy of the compounds. In addition, replacement of the phenyl ring by a chain corresponding to sphingosine yields a strongly inhibitory material. By using a chiral synthetic route, it was discovered that the isomers active against GlcCer synthase had the R,R-(D-threo)-configuration. However, strong inhibition of the growth of human cancer cells in plastico was produced by both the threo and erythro racemic compounds, showing involvement of an additional factor beyond simple depletion of cell glycosphingolipids by blockage of GlcCer synthesis. The growth arresting effects could be correlated with increases in cellular ceramide and diglyceride levels.

Surprisingly, the aliphatic pyrrolidino compound of the present invention (identified as IV-231B), was strongly inhibitory toward the GlcCer synthase and produced almost complete depletion of glycolipids, but did not inhibit growth or cause an accumulation of ceramide. Attempts were made to determine if the differences in growth effects could be attributed to the influence of the inhibitors on related enzymes (ceramide and sphingomyelin synthase and ceramidase and sphingomyelinase). While some stimulation or inhibition of enzyme activity was noted, particularly at high inhibitor concentrations (50 $\mu$M), these findings did not explain the differing effects of the different inhibitors.

By slowing the synthesis of GlcCer, the compounds of the present invention lower the levels of all the GlcCer-derived GSLs due to the GSL hydrolases which normally destroy them. While the body will continue to make the more complex GSLs from available GlcCer, the rate of synthesis will slow down as the level of GlcCer diminishes. The rate of lowering depends on the normal rate of destruction of each GSL. These rates however, are relatively rapid in animals and cultured cells.

At higher dosages, many of the compounds of the present invention produce an elevation in the level of ceramide. Presumably this occurs because cells continue to make ceramide despite their inability to utilize it for GlcCer synthesis. Ceramide is also normally converted to sphingomyelin, but this process does not seem to be able to handle the excess ceramide. It has been unexpectedly found however, that an additional process is also involved, since even those isomers that are inert against GlcCer synthase also produce an elevation in ceramide levels. Moreover, the blockage of GlcCer synthase can occur at low inhibitor dosages, yet ceramide accumulation is not produced. The preferred aliphatic compound of the present invention, D-threo-1-pyrrolidino-1-deoxyceramide (PD), does not produce ceramide accumulation at all, despite almost complete blockage of GlcCer synthesis.

This distinction between the aromatic and the aliphatic compounds of the present invention is important because ceramide has recently been proposed to cause cell death (apoptosis) by some still unknown mechanism. At lower dose levels, the aromatic compounds of the present invention cause GSL disappearance with only small accumulation of ceramide and inhibition of cell growth. Higher dosages cause much more ceramide deposition and very slow cell growth or cell death.

In one embodiment of the present invention, methods of treating patients suffering from inborn genetic errors in the metabolism of GlcCer and its normal anabolic products (lactosylceramide and the more complex GSLs) are provided. The presently known disorders in this category include Gaucher, Fabry, Tay-Sachs, Sandhoff, and GM1 gangliosidosis. The genetic errors lie in the patient's inability to synthesize a hydrolytic enzyme having normal efficiency. Their inefficient hydrolase allows the GSL to gradually accumulate to a toxic degree, debilitating or killing the victim. The compounds of the present invention slow the formation of GSLs, thus allowing the defective hydrolase to gradually "catch up" and restore the concentrations of GSLs to their normal levels and thus the compounds may be administered to treat such patients.

With respect to Gaucher disease, it has been calculated that much of the patient's accumulated GlcCer in liver and spleen arises from the blood cells, which are ultimately destroyed in these organs after they have reached the end of their life span. The actual fraction, lipid derived from blood cells versus lipid formed in the liver and spleen cells, is actually quite uncertain, but the external source must be important. Therefore it is necessary for the compounds of the present invention to deplete the blood cells as they are formed or (in the case of white blood cells) while they still circulate in the blood. Judging from toxicity tests, the white cells continue to function adequately despite their loss of GSLs. Although the toxicity studies were not of a long enough duration to produce many new red cells with low GSL content, it is possible that circulating red cells also undergo turnover (continual loss plus replacement) of GSLs.

In an alternative embodiment of the present invention, for the treatment of disorders involving cell growth and division, high dosages of the compounds of the present invention are administered but only for a relatively short time. These disorders include cancer, collagen vascular diseases, atherosclerosis, and the renal hypertrophy of diabetic patients. Accumulation or changes in the cellular levels of GSLs have been implicated in these disorders and blocking GSL biosynthesis would allow the normal restorative mechanisms of the body to resolve the imbalance.

With atherosclerosis, it has been shown that arterial epithelial cells grow faster in the presence of a GlcCer product (lactosylceramide). Oxidized serum lipoprotein, a material that normally circulates in the blood, stimulates the formation of plaques and lactosylceramide in the inner lining of blood vessels. Treatment with the compounds of the present invention would inhibit this mitogenic effect.

In an additional embodiment of the present invention, patients suffering from infections may be treated with the compounds of the present invention. Many types of pathogenic bacteria have to bind to specific GSLs before they can induce their toxic effects. As shown in Svensson, M. et al., "Epithelial Glucosphingolipid Expression as a Determinant of Bacterial Adherence and Cytokine Production," *Infect. and Immun.* 62:4404–4410 (1994), expressly incorporated by reference, PDMP treatment reduces the adherence of *E. coli* to mammalian cells. Several viruses, such as influenza type A, also must bind to a GSL. Several bacterial toxins, such as the verotoxins, cannot themselves act without first binding to a GSL. Thus, by lowering the level of GSLs, the degree of infection may be ameliorated. In addition, when a patient is already infected to a recognizable, diagnosable degree, the compounds of the present invention may slow the further development of the infection by eliminating the binding sites that remain free.

It has been shown that tumors produce substances, namely gangliosides, a family of GSLs, that prevent the host i.e., patient, from generating antibodies against the tumor. By blocking the tumor's ability to secrete these substances, antibodies against the tumor can be produced. Thus, by administering the GlcCer synthase inhibitors of the present invention to the patient, the tumors will become depleted of their GSLs and the body's normal immunological defenses will come into action and destroy the tumor. This technique was described in Inokuchi, J. et al., "Antitumor Activity in Mice of an Inhibitor of Glycosphingolipid Biosynthesis," *Cancer Lett.* 38:23–30(1987), expressly incorporated by reference. The compounds of the present invention and in particular the aliphatic compounds require much lower doses than those previously described. This is particularly important because the lower dose may reduce certain side effects. Moreover, because the aliphatic compounds of the present invention do not produce ceramide accumulation, they are less toxic. In addition, 1-phenyl-2-palmitoylamino-3-pyrrolidino-1-propanol (P4), may act via two pathways, GSL depletion and ceramide accumulation.

In an alternative embodiment, a vaccine-like preparation is provided. Here, cancer cells are removed from the patient (preferably as completely as possible), and the cells are grown in culture in order to obtain a large number of the cancer cells. The cells are then exposed to the inhibitor for a time sufficient to deplete the cells of their GLSs (generally 1 to 5 days) and are reinjected into the patient. These reinjected cells act like antigens and are destroyed by the patient's immunodefense system. The remaining cancer cells (which could not be physically removed) will also be attacked by the patient's antibodies. In a preferred embodiment, the patient's circulating gangliosides in the plasma are removed by plasmapheresis, since the circulating gangliosides would tend to block the immunodefense system.

It is believed that tumors are particularly dependent on GSL synthesis for maintenance of their growth (Hakomori, S. "New Directions in Cancer Therapy Based on Aberrant Expression of Glycosphingolipids: Anti-adhesion and Ortho-Signaling Therapy," *Cancer Cells* 3:461–470 (1991)). Accumulation of ceramide in treated tumors also slows their growth or kills them. Tumors also generate large amounts of GSLs and secrete them into the patient's body, thereby preventing the host's normal response by immunoprotective cells, which should generate antibodies against or otherwise destroy tumor cells (e.g., tumors are weakly antigenic). It has also been shown that GSL depletion blocks the metastasis of tumor cells (Inokuchi, J. et al., "Inhibition of Experimental Metastasis of Murine Lewis Long Carcinoma by an Inhibitor of Glucosylceramide Synthase and its Possible Mechanism of Action," *Cancer Res.* 50:6731–6737 (1990). Tumor angiogenesis (e.g., the production of blood capillaries) is strongly influenced by GSLs (Ziche, M. et al., "Angiogenesis Can Be Stimulated or Repressed in In Vivo by a Change in GM3:GD3 Ganglioside Ratio," *Lab. Invest.* 67:711–715 (1992)). Depleting the tumor of its GSLs should block the tumors from generating the new blood vessels they need for growth.

A further important characteristic of the compounds of the present invention is their unique ability to block the growth of multidrug resistant ("MDR") tumor cells even at much lower dosages. This was demonstrated with PDMP by Rosenwald, A. G. et al., "Effects of the Glycosphingolipid Synthesis Inhibitor, PDMP, on Lysosomes in Cultured Cells," *J. Lipid Res.* 35:1232 (1994), expressly incorporated by reference. Tumor cells that survive an initial series of therapeutic treatments often reappear some years later with new properties—they are now resistant to a second treatment schedule, even with different drugs. This change has been attributed to the appearance in the tumor of large amounts of a specific MDR protein (P-glycoprotein). It has been suggested that protein kinase C (PKC) may be involved in the action or formation of P-glycoprotein (Blobe, G. C. et al., "Regulation of PKC and Its Role in Cancer Biology," *Cancer Metastasis Rev.* 13:411–431 (1994)). However decreases in PKC have other important effects, particularly slowing of growth. It is known that PDMP does lower the cellular content of PKC (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)) but it is not clear why it so effectively blocks growth of MDR cells (Rosenwald, A. G. et al., "Effects of the Glycosphingolipid Synthesis Inhibitor, PDMP, On Lysosomes in Cultured Cells," *J. Lipid Res.* 35:1232 (1994)). A recent report showed that several lipoidal amines that block MDR action also lower the level of the enzyme acid sphingomyelinase (Jaffrezou, J. et al., "Inhibition of Lysosomal Acid Sphingomyelinase by Agents which Reverse Multidrug Resistance," *Biochim. Biophys. Acta* 1266:1–8 (1995)). One of these agents was also found to increase the cellular content of sphingosine 5-fold, an effect seen with PDMP as well. One agent, chlorpromazine, behaves like the compounds of the present invention, in its ability to lower tissue levels of GlcCer (Hospattankar, A. V. et al., "Changes in Liver Lipids After Administration of 2-Decanoylamino-3-Morpholinopropiophenone and Chlorpromazine," *Lipids* 17:538–543 (1982)).

It will be appreciated by those skilled in the art that the compounds of the present invention can be employed in a wide variety of pharmaceutical forms; the compound can be employed neat or admixed with a pharmaceutically acceptable carrier or other excipients or additives. Generally speaking, the compound will be administered orally or intravenously. It will be appreciated that therapeutically acceptable salts of the compounds of the present invention may also be employed. The selection of dosage, rate/frequency and means of administration is well within the skill of the artisan and may be left to the judgment of the treating physician or attending veterinarian. The method of the present invention may be employed alone or in conjunction with other therapeutic regimens. It will also be appreciated that the compounds of the present invention are also useful as a research tool e.g., to further investigate GSL metabolism.

The following Specific Example further describes the compounds and methods of the present invention.

SPECIFIC EXAMPLE 1

The following formulas set forth preferred aromatic and aliphatic compounds:

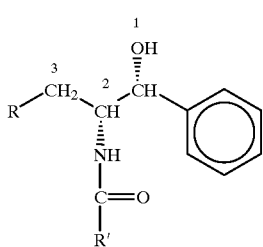

Formula I identified as (1R,2R)-1-phenyl-2-acylamino-3-cyclic amino-1-propanol, and referred to herein as the "aromatic inhibitors," wherein The phenyl group can be a substituted phenyl group (such as p-methoxyphenyl).

R' is an alkyl residue of a fatty acid, 10 to 18 carbons long. The fatty acid can be saturated or unsaturated, or possess a small substitution at the C-2 position (e.g., a hydroxyl group).

R is morpholino, pyrrolidino, piperidino, azetidino (trimethyleneimino), N-methylethanolamino, diethylamino or N-phenylpiperazino. A small substituent, such as a hydroxyl group, is preferably included on the cyclic amine moiety.

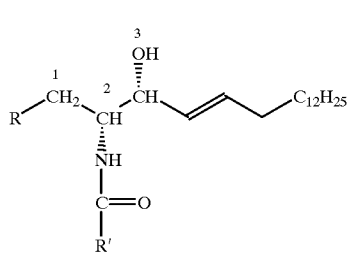

Formula II identified as (2R,3R)-2-palmitoyl-sphingosyl amine or 1-cyclic amino-1-deoxyceramide or 1-cyclic amino-2-hexadecanoylamino-3-hydroxy-octadec-4,5-ene, and referred to herein as the "aliphatic inhibitors," wherein R' is an alkyl residue of a fatty acid, 10 to 18 carbons long. The fatty acid can be saturated or unsaturated, or possess a small substitution at the C-2 position (e.g., a hydroxyl group).

R is morpholino, pyrrolidino, piperidino, azetidino (trimethyleneimino), N-methylethanolamino, diethylamino or N-phenylpiperazino. A small substituent, such as a hydroxyl group, is preferably included on the cyclic amine moiety.

The long alkyl chain shown in Formula II can be 8 to 18 carbon atoms long, with or without a double bond near the asymmetric carbon atom (carbon 3). Hydroxyl groups can, with advantage, be substituted along the aliphatic chain, particularly on carbon 4 (as in the naturally occurring sphingol, phytosphingosine). The long chain can also be replaced by other aliphatic groups, such at t-butyl or cyclopentyl.

The aromatic inhibitors (see Formula I and Table 1) were synthesized by the Mannich reaction from 2-N-acylaminoacetophenone, paraformaldehyde, and a secondary amine as previously described (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987) and Vunnam, R. R. et al., "Analogs of Ceramide that Inhibit Glucocerebroside Synthetase in Mouse Brain," *Chem. Phys. Lipids* 26:265–278 (1980)). For those syntheses in which phenyl-substituted starting materials were used, the methyl group in the acetophenone structure was brominated and converted to the primary amine. Bromination of p-methoxyacetophenone was performed in methanol. The acetophenones and amines were from Aldrich Chemical Co., St. Louis, Mo. Miscellaneous reagents were from Sigma Chemical Co. and the sphingolipids used as substrates or standards were prepared by methods known in the art. The reactions produce a mixture of four isomers, due to the presence of two asymmetric centers.

The aliphatic inhibitors (See Formula II and Table 2) were synthesized from the corresponding 3-t-butyldimethylsilyl-protected sphingols, prepared by enantioselective aldol condensation (Evans, D. A. et al., "Stereoselective Aldol Condensations Via Boron Enolates," *J. Am. Chem. Soc.* 103:3099–3111 (1981) and Abdel-Magid, A. et al., Metal-Assisted Aldol Condensation of Chiral A-Halogenated Imide Enolates: A Stereocontrolled Chiral Epoxide Synthesis," *J. Am. Chem. Soc.* 108:4595–4602 (1986)) using a modification of the procedure of Nicolaou et al. (Nicolaou, K. C. et al., "A Practical and Enantioselective Synthesis of Glycosphingolipids and Related Compounds. Total Synthesis of Globotriaosylceramide ($Gb_3$)," *J. Am. Chem. Soc.* 110:7910–7912 (1988)). Each protected sphingol was first converted to the corresponding primary triflate ester, then reacted with a cyclic amine. Subsequent N-acylation and desilylation led to the final products in good overall yield (Carson, K. G. et al., "Studies on Morpholinosphingolipids: Potent Inhibitors of Glucosylceramide Synthase," *Tetrahedron Lett.* 35:2659–2662 (1994)). The compounds can be called 1-morpholino-(or pyrrolidino)-1-deoxyceramides.

Labeled ceramide, decanoyl sphingosine, was prepared by reaction of the acid chloride and sphingosine (Kopaczyk, K. C. et al., "In Vivo Conversions of Cerebroside and Ceramide in Rat Brain," *J. Lipid Res.* 6:140–145 (1965)) and NBD-SM (12-[N-methyl-N-(7-nitrobenz-2-oxa-1,3-diazol-4-yl)]-sphingosylphosphorylcholine) was from Molecular Probes, Inc., Eugene, Oreg.

Methods

TLC of the amines was carried out with HPTLC plates (E. Merck silica gel 60) and C-M-HOAc 90:10:10 (solvent A) or 85:15:10 (solvent B) or C-M-conc. ammonium hydroxide 30:10:1 (solvent C). The bands were stained with iodine or with Coomassie Brilliant Blue R-250 (Nakamura, K. et al., "Coomassie Brilliant Blue Staining of Lipids on Thin-Layer Plates," *Anal. Biochem.* 142:406–41 (1984)) and, in the latter case, quantified with a Bio-Rad Model 620 videodensitometer operated with reflected white light. The faster band of each PDMP analog, previously identified as the erythro form, corresponds to the 1S,2R and 1R,2S stereoisomers, and the slower band, previously identified as the threo form, corresponds to the 1R,2R and 1S,2S stereoisomers.

TLC of the cell lipids was run with C-M-W 24:7:1 (solvent D) or 60:35:8 (solvent E).

Growth of cell lines. Comparisons of different inhibitors with regard to suppression of human cancer cell growth were made by the University of Michigan Cancer Center in vitro Drug Evaluation Core Laboratory. MCF-7 breast carcinoma cells, HT-29 colon adenocarcinoma cells, H-460 lung large cell carcinoma cells, and 9L brain gliosarcoma cells were grown in RPMI 1640 medium with 5% fetal bovine serum, 2 mM glutamine, 50 units/ml of penicillin, 50 mg/ml of streptomycin, and 0.1 mg/ml of neomycin. UMSCC-10A head and neck squamous carcinoma cells were grown in minimal essential medium with Earle salts and the same supplements. Medium components were from Sigma Chemical Co. Cells were plated in 96-well microtiter plates (1000 cells/well for H-460 and 9L cells, and 2000 cells/well for the other lines), and the test compounds were added 1 day later. The stock inhibitor solutions, 2 mM in 2 mM BSA, were diluted with different amounts of additional 2 mM BSA, then each solution was diluted 500-fold with growth medium to obtain the final concentrations indicated in the Figures and Tables.

Five days after plating the H-460 and 9L cells, or 6 days for the other lines, cell growth was evaluated by staining the adhering cells with sulforhodamine B and measuring the absorbance at 520 nm (Skehan, P. et al., "New Colorimetric Cytotoxicity Assay for Anticancer-Drug Screening," *J. Natl. Cancer Inst.* 82:1107–1112 (1990)). The absorbance of the treated cultures is reported as percent of that of control cultures, to provide an estimate of the fraction of the cells that survived, or of inhibition of growth rate.

For the experiments with labeled thymidine, each 8.5 cm dish contained 500,000 Madin-Darby canine kidney (MDCK) cells in 8 ml of Dulbecco modified essential supplemented medium. The cells were incubated at 37° C. in 5% $CO_2$ for 24 h, then incubated another 24 h with medium containing the inhibitor-BSA complex. The control cells were also incubated in the presence of BSA. The cells were washed with phosphate/saline and trichloroacetic acid, then scraped off the dishes, dissolved in alkali, and analyzed for protein and DNA incorporated tritium. [Methyl-$^3$H] thymidine (10 $\mu$Ci) was added 4 h prior to harvesting.

Assay of sphingolipid enzymes.

The inhibitors were evaluated for their effectiveness against the GlcCer synthase of MDCK cell homogenates by incubation in a thermostatted ultrasonic bath (Radin N. S. et al., "Ultrasonic Baths as Substitutes for Shaking Incubator Baths," *Enzyme* 45:67–70 (1991)) with octanoyl sphingosine and uridinediphospho[$^3$H]glucose (Shukla, G. S. et al., "Glucosylceramide Synthase of Mouse Kidney: Further Characterization and Improved Assay Method," *Arch. Biochem. Biophys.* 283:372–378 (1990)). The lipoidal substrate (85 $\mu$g) was added in liposomes made from 0.57 mg dioleoylphosphatidylcholine and 0.1 mg of Na sulfatide. Confluent cells were washed, then homogenized with a micro-tip sonicator at 0° C. for 3×30 sec; ~0.2 mg of protein was used in each assay tube. In the case of the aromatic inhibitors, the test compound was simply evaporated to dryness from solution in the incubation tube. This method of adding the inhibitor was found to give the same results as addition as a part of the substrate liposomes. The aliphatic inhibitors, which appeared to be less soluble in water, were added as part of the substrate liposomes.

Acid and neutral ceramidases were assayed under conditions like those above, but the medium contained 110 $\mu$M [1-$^{14}$C]decanoyl sphingosine ($10^5$ cpm) in 340 $\mu$M dioleoylphosphatidylcholine liposomes and 0.34 mg of MDCK cellular protein homogenate. The acid enzyme was incubated in 32.5 mM citrate-Na$^+$ (pH 4.5) and the neutral enzyme buffer was 40 mM Tris-Cl$^-$ (pH 7.1 at 37° C.). After 60 min in the ultrasonic bath, 3 ml of C-M 2:1, carrier decanoic acid, and 0.6 ml of 0.9% saline were added and the lipids in the lower layer were separated by TLC with C-HOAc 9:1. The liberated decanoic acid was scraped off the glass plate and counted.

Ceramide synthase was assayed with 1 $\mu$M [3-$^3$H] sphingosine (70,000 cpm, repurified by column chromatography), 0.2 mM stearoyl-CoA, 0.5 mM dithiothreitol, and ~300 $\mu$g of MDCK homogenate protein in 25 mM phosphate-K$^+$ buffer, pH 7.4, in a total volume of 0.2 ml. The incubation (for 30 min) and TLC were carried out as above and the ceramide band was counted.

Sphingomyelin synthase was evaluated with 44 $\mu$M [$^{14}$C] decanoyl sphingosine ($10^5$ cpm) dispersed with 136 $\mu$M dioleoyllecithin as in the ceramide synthase assay, and 5 mM EDTA and 50 mM Hepes-Na$^+$ pH 7.5, in a total volume of 0.5 ml. MDCK homogenate was centrifuged at 600×g briefly, then at 100,000×g for 1 h, and the pellet was suspended in water and sonicated with a dipping probe. A portion of this suspension containing 300 $\mu$g of protein was used. Incubation was at 37° C. for 30 min, after which the lipids were treated as above, using C-M-W 60:35:8 for the isolation of the labeled decanoyl SM.

Acid and neutral SMase assays were based on the procedures of Gatt et al. (Gatt, S. et al., "Assay of Enzymes of Lipid Metabolism With Colored and Fluorescent Derivatives of Natural Lipids," *Meth. Enzymol.* 72:351–375 (1981)), using liposomes containing NBD-SM dispersed like the labeled ceramide (10 $\mu$M substrate and 30 $\mu$M lecithin). The assay medium for the neutral enzyme also contained 50 mM Tris-Cl$^-$(pH 7.4), 25 mM KCl, 5 mM MgCl$_2$ and 0.29 mg of MDCK cell protein in a total volume of 0.25 ml. Incubation was at 37° C. for 30 min in the ultrasonic bath, then the fluorescent product, NBD-ceramide, was isolated by partitioning the assay mixture with 0.45 ml 2-propanol, 1.5 ml heptane, and 0.2 ml water. After centrifugation, a trace of contaminating NBD-SM was removed from 0.9 ml of the upper layer by washing with 0.35 ml water. The upper layer was analyzed with a fluorometer (460 nm excitation, 515 nm emission).

Acid SMase was assayed with the same liposomes in 0.2 ml of assay mixture containing 125 mM NaOAc (pH 5.0) and 61 $\mu$g of cell protein, with 60 min of incubation at 37° C. The resultant ceramide was determined as above.

Results

Table 1 lists the aromatic compounds (see Formula I) synthesized and their migration rates on silica gel TLC plates. Separation of the threo- and erythro-steroisomers by TLC was generally very good, except for BML-120, -121, and -122 in the acidic solvent. In the basic solvent BML-119 and BML-122 yielded poorly resolved double bands. BML-112 was unexpectedly fast-running, especially when compared with BML-120; both are presumably dihydrochlorides.

TABLE 1

Structures of the Aromatic Inhibitors

| BML Number or Name | R Group | Phenyl Substituent | TLC hR$_f$ Value[a] |
|---|---|---|---|
| PDMP[b] | morpholino | | 34(47) |
| PPMP | morpholino | | (53) |
| 112 | N-phenylpiperazino | | 56 |
| 113 | morpholino | p-fluoro | 25 |
| 114 | diethylamino | | 25 |
| 115 | piperidino (pentamethyleneimino) | | 29 |
| 116 | hexamethyleneimino | | 34 |
| 117[b] | morpholino | p-fluoro | 41 |
| 118 | piperidino | p-fluoro | 26 |
| 119 | pyrrolidino (tetramethyleneimino) | | 20–70(44) |
| 120 | 1-methylpiperazino | | 7–62 |
| 121 | 3-dimethylaminopiperidino | | 1–30 |
| 122 | N-methylethanolamino | | 6–71 |
| 123 | azetidino (trimethyleneimino) | | 12 |
| 124 | amino | | 15 |
| 125 | morpholino | p-methoxy | 37 |
| 126 | pyrrolidino | p-methoxy | (50) |

[a]Only the relative R$_f$ value of the faster-moving band is shown. The first value was obtained with solvent A, the second with solvent C, and the numbers in parentheses, with solvent B. In the case of BML-117, –125, and –126, a 20-cm high TLC plate was used to improve the seperation.
[b]The fatty acid chain suggested by the R' group is decanoyl, not palmitoyl.

Table 2 describes four aliphatic inhibitors (see Formula II), which can be considered to be ceramide analogs in which the C-1 hydroxyl group is replaced by a cyclic amine. It should be noted that the carbon frameworks of compounds in Tables 1 and 2 are numbered differently (see Formulas I and II), thus affecting comparisons of stereochemical configurations. The threo- and erythro-isomers separated very poorly on TLC plates. Like the aromatic inhibitors, however, the morpholine compounds ran faster than the pyrrolidine compounds. The latter are presumably more strongly adsorbed by the silica gel because they are more basic.

TABLE 2

Characterization of the Sphingosyl Inhibitors

| Number | R Group | Sphingol Structure | TLC hR$_f$ Value[a] |
|---|---|---|---|
| IV-181A | morpholino | 2R,3S | 43 |
| IV-206A | morpholino | 2R,3R | 40 |
| IV-230A | pyrrolidino | 2R,3S | 31 |
| IV-231B | pyrrolidino | 2R,3R | 31 |

[a]TLC solvent: C-M-HOAc 90:5:10. Similar but faster migrations were obtained with solvent A.

Structure-activity correlations. The results of testing the compounds in an assay system for GlcCer synthase are listed in Table 3. Each inhibition determination (±SD) shown in Table 3 was carried out in triplicate. Some of the inhibitors were tested as mixtures of DL-erythro- and DL-threo-isomers (see column 4). Only the D-threo enantiomer in each mixture was predicted to be the actual enzyme inhibitor (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987)); the content of this isomer was calculated by measuring the proportions of the threo- and erythro-racemic mixtures by quantitative TLC. The DL-threo contents were found to be in the range of 40 to 72%. The comparisons, in the case of the mixtures, are therefore approximate (most of the samples were not purified to remove the three less-active isomers and the observed data were not corrected for the level of the primary enantiomers). The separation of the threo- and erythro-forms is most conveniently accomplished by crystallization, but the specific conditions vary for each substance; thus only BML-119, a strong inhibitor, was separated into its threo- and erythro-forms. BML-112 is not included in Table 3 because it had no inhibitory activity against GlcCer synthase of rabbit liver microsomes.

TABLE 3

Inhibition of Ceramide Glucosyltransferase of MDCK cell Homogenates by Different Compounds

| Inhibitor Number | % Inhibition at 80 μM | Inhibition at 5 μM | Active Isomer[h] |
|---|---|---|---|
| BML-113 | 60 ± 4.7[a] | | 29 |
| BML-114 | 31 ± 2.9[a] | | 20 |
| BML-115 | 84 ± 0.8[a] | 12.4 ± 0.7[f] | 27 |
| | 82 ± 0.3[b] | | |
| BML-116 | 28 ± 3.2[a] | | 27 |
| BML-117 | 35 ± 0.6[b] | | 36 |
| BML-118 | 62 ± 0.4[b] | 8.3 ± 1.4[f] | 32 |
| BML-119 | 94 ± 1.4[b] | 51 ± 2.3[e] | 29 |
| | 97 ± 0.1[c] | 49 ± 0.8[f] | |
| | 96 ± 0.1[d] | | |
| BML-120 | 11 ± 3.0[c] | | 26 |
| BML-121 | 11 ± 0.4[c] | | 28 |
| BML-122 | 58 ± 1.6[d] | | 26 |
| BML-123 | 86 ± 0.1[d] | 15 ± 0.8[f] | 33 |
| BML-124 | –2 ± 1.6[d] | | 15 |
| BML-125 | | 9 ± 3.0[e] | 26 |
| BML-126 | 60 ± 1.8[e] | 54 ± 0.3[f] | 34 |
| PDMP | 90 ± 0.8[a] | 16 ± 1.8[e] | 100 |
| PPMP | | 32 ± 1.8[e] | 100 |
| | | 32 ± 0.7[f] | |
| IV-181A | | 12 ± 0.2[g] | 100 |
| IV-206A | | 73 ± 1.5[g] | 100 |
| IV-230A | | 19 ± 2.1[g] | 100 |
| IV-231B | | 87 ± 0.4[g] | 100 |

[a–g]Different samples were assayed as parts of different experiments.
[h]Percent of the active D-stereoisomer in the synthesized sample, estimated by scanning the two stained bands, assuming the slower one was the (racemic) active form.

Comparison of PDMP (1R,2R-decanoate) and PPMP (1R, 2R-palmitate), when evaluated at the same time in Expt. f, shows that an increase in the chain length of the N-acyl group from 10 to 16 carbon atoms distinctly improved the inhibitory activity against GlcCer synthase, as noted before (Abe, A. et al., "Improved Inhibitors of Glucosylceramide Synthesis," *J. Biochem.* 111:191–196 (1992)). Accordingly, most of the other compounds were synthesized with the palmitoyl group for comparison with PPMP. The comparisons between the best inhibitors are clearer at the 5 μM level.

Replacing the oxygen in the morpholine ring of PPMP with a methylene group (BML-115) improved activity ~1.4-fold (calculated from the inhibitions at 5 μM in Expt. f and relative purities, and assuming that the percent inhibition is proportional to concentration in this region: 12.4/27×100/ 32=1.4). Previous comparison with mouse brain, human placenta, and human Gaucher spleen glucosyltransferase also showed that replacing the morpholino ring with the piperidino ring in a ketone analog of PDMP (1-phenyl-2-decanoylamino-3-piperidino-1-propanone) produced a much more active inhibitor (Vunnam, R. R. et al., "Analogs of Ceramide that Inhibit Glucocerebroside Synthetase in Mouse Brain," *Chem. Phys. Lipids* 26:265–278 (1980)).

Replacing the piperidine group with a 7-membered ring (BML-116) greatly decreased the activity, while use of a 5-membered ring (BML-119) quadrupled the effectiveness (50 vs 12.4% inhibition). A 4-membered ring (BML-123)

yielded a compound about as effective as the piperidino compound. The parent amine (BML-124), its N,N-diethyl analog (BML-114), and the sterically bulky N-phenylpiperazine analog (BML-112) displayed little or no activity.

Replacing a hydrogen atom with a fluorine atom in the p-position of the phenyl ring decreased the inhibitory power (BML-117 vs PDMP and BML-118 vs BML-115). Substitution of the p-position with an electron-donating moiety, the methoxy group, had a similar weakening effect in the case of the morpholino compound (BML-125 vs PPMP). Comparison of the pyrrolidino compounds, which are more basic than the morpholino compounds, showed that the methoxy group enhanced the inhibitory power (BML-126 vs BML-119).

Preparations of BML-119 were separated into threo and erythro racemic mixtures by HPLC on a Waters Microbondapak $C_{18}$ column, using M-W-conc. $NH_4OH$ 90:10:0.2 as the elution solvent. The material eluting earlier (but migrating more slowly on a TLC plate) was called BML-130; the later eluting material (faster by TLC) was called BML-129. Assay of GlcCer synthase with each preparation at 5 $\mu$M showed 15% inhibition by BML-129 and 79% inhibition by BML-130. TLC analysis of the two preparations revealed incomplete separation, which could explain the minor inhibition by BML-129. When the two stereoisomers were separated by preparative TLC, the difference in effectiveness was found to be somewhat higher, evidently due to the better separation by this method. Thus the slower-migrating stereoisomer accounted for all or nearly all of the inhibitory activity, as noted with PDMP (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987)).

Comparison of the two pairs of aliphatic inhibitors (bottom of Table 3) showed that the 2R,3R (D-threo) form is the primary inhibitor of glucosyltransferase. This finding is in agreement with previous identification of the active PDMP isomer as being the D-threo enantiomer. However, unlike the aromatic analog, BML-129 (2R,3S/2S,3R), there was a relatively small but significant activity in the case of the (erythro) 2R,3S stereoisomer. The erythro form of PDMP was found to inhibit cell proliferation of rabbit skin fibroblasts almost as well as R,R/S,S-PDMP but it did not act on the GSLs (Uemura, K. et al., "Effect of an Inhibitor of Glucosylceramide Synthesis on Cultured Rabbit Skin Fibroblasts," *J. Biochem.* (Tokyo) 108:525–530 (1990)). As noted with the aromatic analogs, the pyrrolidine ring was more effective than the morpholine ring (Table 3).

Comparison of the aliphatic and corresponding aromatic inhibitors can be made in the case of the optically active morpholine compounds PPMP and IV-206A, both of which have the R,R structure and the same fatty acid. Here it appears that the aliphatic compound is more effective (Table 3). However in a second comparison, at lower concentrations with the inhibitors incorporated into the substrate liposomes, the degree of inhibition was 77±0.9% with 3 $\mu$M IV-231B and 89±0.6% with 6 $\mu$M DL-threo BML-119.

Evaluations of cultured cell growth. Exposure of five different cancer cell lines to inhibitors at different concentrations for 4 or 5 days showed that the six BML compounds most active against GlcCer synthase were very effective growth inhibitors (Table 4). The $IC_{50}$ values (rounded off to one digit in the table) ranged from 0.7 to 2.6 $\mu$M.

TABLE 4

Inhibition of Tumor Cell Growth In Vitro by Various Inhibitors

| Cell Type | BML-115 | BML-118 | BML-119 | BML-123 | BML-126 | BML-129 | BML-130 |
|---|---|---|---|---|---|---|---|
| MCF-7 | 2 | 2 | 2 | 2 | 1 | 3 | 2 |
| H-460 | 2 | 2 | 1 | 1 | 1 | 2 | 3 |
| HT-29 | 2 | | 1 | 2 | 1 | 2 | 2 |
| 9L | 2 | 2 | 1 | 2 | 2 | 2 | 2 |
| UMSCC-10A | 1 | | 1 | 1 | 1 | 2 | 2 |

FIG. 1 shows growth and survival of 9L gliosarcoma cells grown in medium containing different GlcCer synthase inhibitors, as described above. The BML compounds were used as synthesized (mixtures of DL-threo and -erythro stereoisomers) while the PDMP and PPMP were optically resolved R,R isomers. The concentrations shown are for the mixed racemic stereoisomers, since later work (Table 4) showed that both forms were very similar in effectiveness. FIG. 1 illustrates the relatively weak effectiveness of R,R-PPMP and even weaker effectiveness of R,R-PDMP. The three new compounds, however, are much better inhibitors of GlcCer synthase and growth. These differences in growth inhibitory power correlate with their effectiveness in MDCK cell homogenates as GlcCer synthase inhibitors. Some differences can be expected due to differences in sensitivity of the synthase occurring in each cell type (the synthases were assayed only in MDCK cells).

Growth inhibition by each of the most active BML compounds occurred in an unusually small range of concentrations (e.g., the slopes of the cytotoxic regions are unusually steep). Similar rapid drop-offs were seen in another series of tests with 9L cells, in which BML-119 yielded 71% of the control growth with 1 $\mu$M inhibitor, but only 3% of control growth with 3 $\mu$M. Growth was 93% of control growth with 2 $\mu$M BML-130 but only 5% of controls with 3 $\mu$M inhibitor. While some clinically useful drugs also show a narrow range of effective concentrations, this is a relatively uncommon relationship.

When the erythro- and threo-stereoisomeric forms of BML-119 (-129 and -130) were compared, they were found to have similar effects on tumor cell growth (Table 4). This observation is similar to the results with PDMP isomers in fibroblasts cited above (Uemura, K. et al., "Effect of an Inhibitor of Glucosylceramide Synthesis on Cultured Rabbit Skin Fibroblasts," *J. Biochem.* (Tokyo) 108:525–530 (1990)). Since enzymes are optically active and since stereoisomers and enantiomers of drugs can differ greatly in their effect on enzymes, it is likely that BML-129 and BML-130 work on different sites of closely related metabolic steps.

Figure 2:
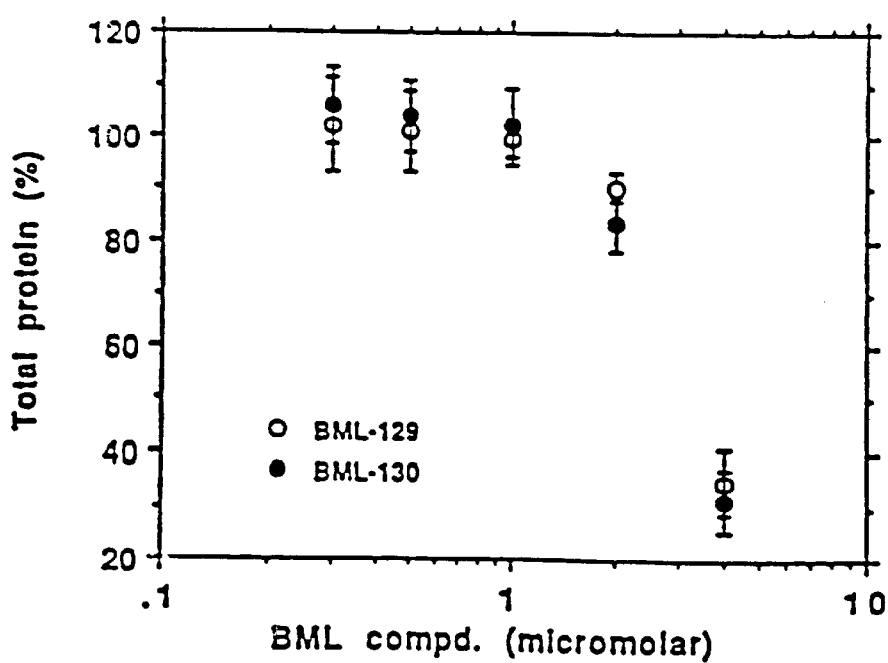
FIG. 2 is a graph showing the protein content of MDCK cells cultured for 24 hr in medium containing different concentrations of the separated erythro- and threo-isomers of a preferred compound of the present invention.

FIG. 2 shows the amount of cellular protein per dish for MDCK cells cultured for 24 h in medium containing different concentrations of the separated erythro- and threo-isomers of BML-119, as percent of the incorporation by cells in standard medium. Each point shown in FIG. 2 is the average of values from three plates, with error bars corresponding to one standard deviation.

Figure 3:
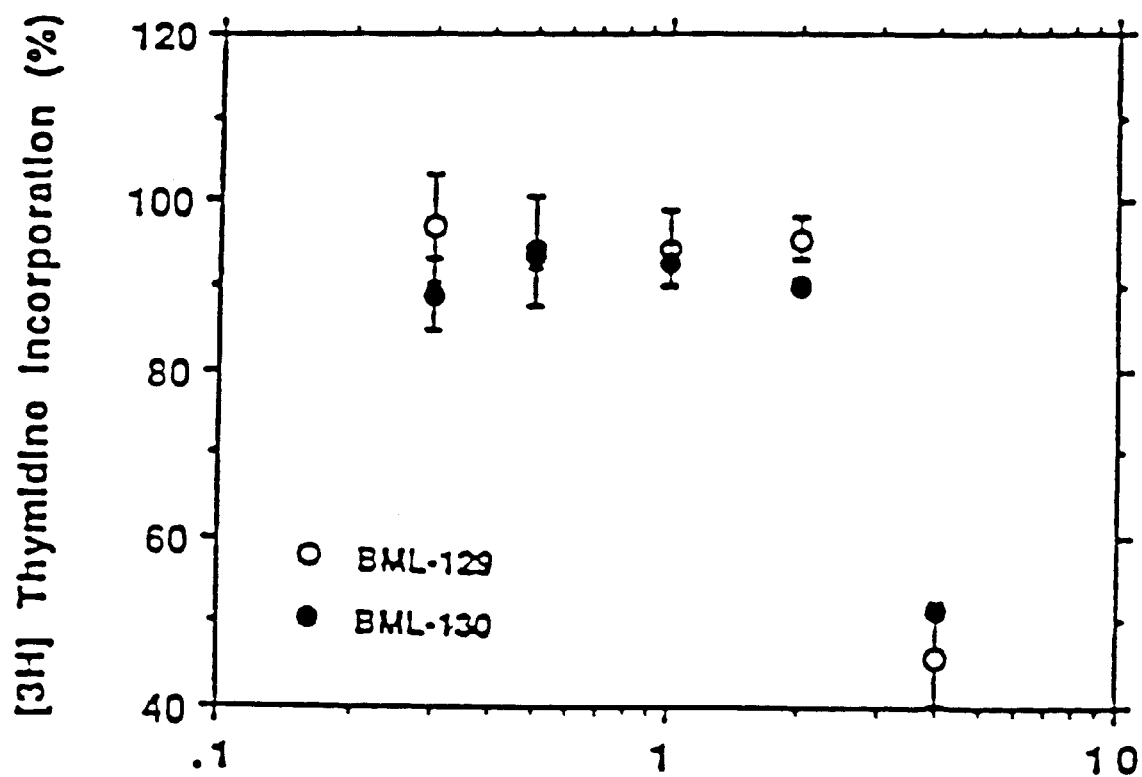
FIG. 3 is a graph showing [$^3$H]thymidine incorporation into the DNA of MDCK cells treated with a preferred compound of the present invention.

FIG. 3 shows [$^3$H]thymidine incorporation into DNA of MDCK cells incubated as in FIG. 2. The values in FIG. 3 are normalized on the basis of the protein content of the incubation dishes and compared to the incorporation by cells in standard medium.

FIGS. 2 and 3 thus provide comparison of the two stereoisomers with MDCK cells. The isomers were found to inhibit growth and DNA synthesis with similar effectiveness. Thus the MDCK cells behaved like the human tumor cells with regard to IC$_{50}$ and the narrow range of concentrations resulting in inhibition of protein and DNA synthesis.

Surprisingly, the aliphatic inhibitor IV-231B exerted no inhibitory effect on MDCK cell growth when incubated at 20 $\mu$M for 1 day or 1 $\mu$M for 3 days. Tests with a longer growth period, 5 days, in 5 $\mu$M inhibitor also showed no slowing of growth. The dishes of control cells, which contained BSA as the only additive to the medium, contained 3.31±0.19 mg of protein, while the IV-231B/BSA treated cells contained 3.30±0.04 mg.

Lipid changes induced in the cells. Examination by TLC of the alkali-stable MDCK lipids after a 24 h incubation disclosed that BML-130 was more effective than BML-129 in lowering GlcCer levels, as expected from its greater effectiveness in vitro as a glucosyltransferase inhibitor. The level of GlcCer, estimated visually, was greatly lowered by 0.3 $\mu$M BML-130 or 0.5 $\mu$M BML-129. The levels of the other lipids visible on the plate (mainly sphingomyelin (SM), cholesterol, and fatty acids) were changed little or not at all. BML-129 and the GlcCer synthase inhibitor, BML-130, were readily detected by TLC at the various levels used, showing that they were taken up by the cells during the incubation period at dose-dependent rates. Lactosylceramide overlapped the inhibitor bands with solvent D but was well separated with solvent E, which brought the inhibitors well above lactosylceramide.

Ceramide accumulation was similar for both stereoisomers (data not shown). An unexpected finding is that noticeable ceramide accumulation appeared only at inhibitor concentrations that were more than enough to bring GlcCer levels to a very low point (e.g., at 2 or 4 $\mu$M). The changes in ceramide concentration were quantitated in a separate experiment by the diglyceride kinase method, which allows one to also determine diacylglycerol (DAG) concentration (Preiss, J. E. et al., "Quantitative Measurement of SN-1,2-Diacylglycerols Present in Platelets, Hepatocytes, and Ras- and Sis-Transformed Normal Rat Kidney Cells," *J. Biol. Chem.* 261:8597–8600 (1986)). The results (Table 5) are similar to the visually estimated ones: at 0.4 $\mu$M BML-129 or -130 there was little effect on ceramide content but at 4 $\mu$M inhibitor, a substantial increase was observed. (While the duplicate protein contents per incubation dish were somewhat erratic in the high-dose dishes, in which growth was slow, the changes were nevertheless large and clear.) Accumulation of ceramide had previously been observed with PDMP, at a somewhat higher level of inhibitor in the medium (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). From the data for cellular protein per incubation dish, it can be seen that there was no growth inhibition at the 0.4 $\mu$M level with either compound but substantial inhibition at the 4 $\mu$M level, especially with the glucosyltransferase inhibitor, BML-130. This finding is similar to the ones made in longer incubations with human cancer cells.

TABLE 5

Effects of BML-129 and -130 on MDCK Cell Growth and the Content of Ceramide and Diacylglycerol

| Growth Medium | Protein $\mu$g/dish | Ceramide nmol/mg protein | Diglyceride nmol/mg protein |
| --- | --- | --- | --- |
| Controls | 490 | 1.04 | 4.52 |
|  | 560 | 0.96 | 5.61 |
| 0.4 $\mu$m BML-129 | 500 | 1.29 | 5.51 |
|  | 538 | 0.99 | 5.13 |
| 0.4 $\mu$m BML-130 | 544 | 0.94 | 4.73 |
|  | 538 | 0.87 | 5.65 |
| 4 $\mu$m BML-129 | 396 | 3.57 | 9.30 |
|  | 311 | 3.78 | 9.68 |
| 4 $\mu$m BML-130 | 160 | 5.41 | 11.9 |
|  | 268 | 3.34 | 8.71 |

In a separate study of ceramide levels in MDCK cells, BML-130 at various concentrations was incubated with the cells for 24 h. The ceramide concentration, measured by TLC densitometry, was 1.0 nmol/mg protein at 0.5 $\mu$M, 1.1 at 1 $\mu$M, 1.5 at 2 $\mu$M, and 3.3 at 4 $\mu$M. The results with BML-129 were virtually identical.

It is interesting that the accumulation of ceramide paralleled an accumulation of diacylglycerol (DAG), as observed before with PDMP (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). DAG is ordinarily considered to be an activator of protein kinase C and thus a growth stimulator, but the low level of GlcCer in the inhibited cells may counteract the stimulatory effect. Ceramide reacts with lecithin to form SM and DAG, so it is possible that the increased level of the latter reflects enhanced synthesis of the phosphosphingolipid rather than an elevated attack on lecithin by phospholipase D. Arabinofuranosylcytosine (ara-C), an antitumor agent, also produces an elevation in the DAG and ceramide of HL-60 cells (Strum, J. C. et al., "1-$\beta$-D-Arabinofuranosylcytosine Stimulates Ceramide and Diglyceride Formation in HL-60 Cells," *J. Biol. Chem.* 269:15493–15497 (1994)).

TLC of MDCK cells grown in the presence of 0.02 to 1 $\mu$M IV-231B for 3 days showed that the inhibitor indeed penetrated the cells and that there was a great depletion of GlcCer, but no ceramide accumulation. The depletion of GlcCer was evident even at the 0.1 $\mu$M level and virtually no GlcCer was visible at the 1 $\mu$M level; however the more polar GSLs were not affected as strongly. After incubation for 5 days in 5 $\mu$M inhibitor, all the GSLs were virtually undetectable. The ceramide concentrations in the control and depleted cells were very similar: 13.5±1.4 vs 13.9±0.2 $\mu$g/mg protein.

The lack of ceramide accumulation in cells exposed to the aliphatic inhibitors was examined further to see if it might be due to differential actions of the different inhibitors on additional enzymes involving ceramide metabolism. For example, IV-231B might block ceramide synthase and thus prevent accumulation despite the inability of the cells to utilize ceramide for GlcCer synthesis. However, assay of ceramide synthase in homogenized cells showed it was not significantly affected by 5 µM inhibitors (Table 6). There did appear to be moderate inhibition at the 50 µM level with PDMP and the aliphatic inhibitor.

TABLE 6

Effect of Inhibitors on Acid and Neutral Ceramidases and Ceramide Synthase of MDCK Cells

| Inhibitor Tested | Enzyme Activity (% of control) | | |
|---|---|---|---|
| | Ceramidase pH 4.5 | Ceramidase pH 7.4 | Ceramide Synthase |
| D-threo-PDMP, 5 µM | 97 ± 4 | 116 ± 19 | 99 ± 5 |
| D-threo-PDMP, 50 µM | 133 ± 13[a] | 105 ± 11 | 66 ± 9[a] |
| BML-129, 5 µM | 108 ± 8 | 100 ± 0 | 97 ± 0 |
| BML-129, 50 µM | 171 ± 26[a] | 99 ± 2 | 102 ± 1 |
| BML-130, 5 µM | 107 ± 11 | 100 ± 15 | 108 ± 10 |
| BML-130, 50 µM | 160 ± 21[a] | 100 ± 15 | 106 ± 29 |
| IV-231B, 5 µM | 106 ± 3 | 116 ± 20 | 90 ± 8 |
| IV-231B, 50 µM | 113 ± 8 | 112 ± 3 | 71 ± 18[a] |

[a]Notable differences.

Assay of the two kinds of ceramidase (Table 6) showed that there was no effect of either the aliphatic or aromatic inhibitors at the 5 µM level, at which point cell growth is completely stopped in the case of the pyrrolidino compounds. At the 50 µM level, however, the acid enzyme was stimulated markedly by the aromatic inhibitors, particularly the two stereoisomeric forms of the pyrrolidino compound.

Sphingomyelin synthase was unaffected by PDMP or the aliphatic inhibitor but BML-129 and -130 produced appreciable inhibition at 50 µM (54% and 61%, respectively) (Table 7).

TABLE 7

Effect of Inhibitors on Acid and Neutral Sphingomyelinases and Sphingomyelin Synthase

| Inhibitor Tested | Enzyme Activity (% of control) | | |
|---|---|---|---|
| | Sphingomyelinase pH 4.5 | Sphingomyelinase pH 7.1 | Sphingomyelinase Synthase[a] |
| D-threo-PDMP, 5 µM | 102 ± 3 | 121 ± 13 | |
| D-threo-PDMP, 50 µM | 100 ± 3 | 108 ± 8 | |
| BML-129, 5 µM | 108 ± 4 | 105 ± 11 | 84 ± 27 |
| BML-129, 50 µM | 97 ± 3 | 142 ± 11[b] | 46 ± 11[b] |
| BML-130, 5 µM | 109 ± 1 | 110 ± 7 | 87 ± 14 |
| BML-130, 50 µM | 114 ± 2 | 152 ± 14[b] | 39 ± 18[b] |
| IV-231B, 5 µM | 101 ± 7 | 131 ± 3[b] | |
| IV-231B, 50 µM | 112 ± 11 | 120 ± 3[b] | |

[a]Data for PDMP and IV-231B are not shown here as they were tested in other experiments; no effect was seen.
[b]Notable differences.

Neutral sphingomyelinase (SMase) was distinctly stimulated by the aliphatic inhibitor, IV-231B, even at 5 µM (Table 7). From this one would expect that the inhibitor would produce accumulation of ceramide, yet it did not. The two pyrrolidino compounds produced appreciable stimulation at the 50 µM level. No significant effects were obtained with acid SMase.

Discussion

The present invention shows that the nature and size of the tertiary amine on ceramide-like compounds exerts a strong influence on GlcCer synthase inhibition, a 5-membered ring being most active. It also shows that the phenyl ring used previously to simulate the trans-alkenyl chain corresponding to that of sphingosine could, with benefit, be replaced with the natural alkenyl chain.

Findings with the most active GlcCer synthase inhibitors in growth tests compare favorably with evaluations of some clinically useful chemotherapeutic agents on three of the tumor cell lines in the same Drug Evaluation Core Laboratory. The $IC_{50}$ values were 0.2 to 6 µM for cisplatin, 0.02 to 44 µM for carboplatin, 0.03 to 0.2 µM for methotrexate, 0.07 to 0.2 µM for fluorouracil, and 0.1 to 1 µM for etoposide. Unlike these agents, the compounds of the present invention yielded rather similar effects with all the cell types, including MDCK cells, and thus have wider potential chemotherapeutic utility. This uniformity of action is consistent with the idea that GSLs play a wide and consistent role in cell growth and differentiation.

An important observation from the MDCK cell study is that strong inhibition of cell growth and DNA synthesis occurred only at the same concentrations of aromatic inhibitor that produced marked ceramide accumulation. This observation supports the assertion that ceramide inhibits growth and enhances differentiation or cell death (Bielawska, A. et al., "Modulation of Cell Growth and Differentiation by Ceramide," *FEBS Letters* 307:211–214 (1992)). It also agrees with previous work with octanoyl sphingosine, a short chain ceramide that produced greatly elevated levels of natural ceramide and slowed growth (Abe, A. et al., "Metabolic Effects of Short-Chain Ceramide and Glucosylceramide on Sphingolipids and Protein Kinase C," *Eur. J. Biochem.* 210:765–773 (1992)). It is also in agreement with a finding that some synthetic, nonionic ceramide-like compounds did not inhibit GlcCer synthase even though they behave like ceramide in blocking growth (Bielawska, A. et al., "Ceramide-Mediated Biology. Determination of Structural and Stereospecific Requirements Through the Use of N-Acyl-Phenylaminoalcohol Analogs," *J. Biol. Chem.* 267:18493–18497 (1992)). Compounds tested included 20 µM D-erythro-N-myristoyl-2-amino-1-phenyl-1-propanol, its L-enantiomer, the four stereoisomers of N-acetylsphinganine, and N-acetylsphingosine. Furthermore, the lack of growth inhibition and ceramide accumulation in cells treated with the aliphatic inhibitor IV-231B is also consistent with the correlation between ceramide level and growth rate.

The accumulation of ceramide that occurred at higher levels of GlcCer synthase inhibitors could be attributed not only to blockage of ceramide utilization, but also to blockage of SM synthesis or ceramide hydrolase. This possibility is especially relevant to the R,S-, S,R-, and S,S-isomers, which seem to exert effects on sphingolipids without strongly inhibiting GlcCer synthesis. The tests with both the DL-erythro-pyrrolidino inhibitor (BML-129) and the DL-threo-pyrrolidino inhibitor (BML-130), at a level producing strong growth inhibition, showed that neither material at a low concentration inhibited the enzymes tested in vitro (Tables 6 and 7) but they did cause growth inhibition as well as accumulation of ceramide. PDMP, at relatively high concentrations (50 µM), was found to inhibit SM synthase in growing CHO cells (Rosenwald, A. G. et al., "Effects of a Sphingolipid Synthesis Inhibitor on Membrane Transport Through the Secretory Pathway," *Biochemistry*

31:3581–3590 (1992)). In the test with MDCK homogenates, it did not inhibit this synthase, in agreement with the finding that labeled palmitate incorporation into SM was stimulated by PDMP (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)).

Retinoic acid is a growth inhibitor of interest in cancer chemotherapy and a possible adjunct in the use of the inhibitors of the present invention. It has been found to elevate ceramide and DAG levels (Kalen, A. et al., "Elevated Ceramide Levels in GH4C1 Cells Treated with Retinoic Acid," *Biochim. Biophys. Acta* 1125:90–96 (1992)) and possibly lower lecithin content (Tang, W. et al., "Phorbol Ester Inhibits 13-Cis-Retinoic Acid-induced Hydrolysis of Phosphatidylinositol 4,5-Bisphosphate in Cultured Murine Keratinocytes: a Possible Negative Feedback Via Protein Kinase C-Activation," *Cell Bioch. Funct.* 9:183–191 (1991)).

D-threo-PDMP was found to be rather active in delaying tumor cell growth or in producing complete cures in mice (Inokuchi, J. et al., "Antitumor Activity in Mice of an Inhibitor of Glycosphingolipid Biosynthesis," *Cancer Lett.* 38:23–30 (1987)) but high doses were needed. From the data in FIG. 1, the inhibitors of the present invention are approximately 30 times as active, so the dosage levels are typical of clinically useful drugs. The need to use high doses with PDMP was attributed to rapid inactivation by cytochrome P450 (Shukla, A. et al., "Metabolism of D-[$^3$H]PDMP, an Inhibitor of Glucosylceramide Synthesis, and the Synergistic Action of an Inhibitor of Microsomal Monooxygenase," *J. Lipid Res.* 32:713–722 (1991)). Cytochrome P450 can be readily blocked by various nontoxic drugs such as cimetidine, therefore high levels of the compounds of the present invention can be maintained.

SPECIFIC EXAMPLE 2

A series of inhibitors based on substitutions in the phenyl ring of P4 were synthesized and studied. It was found that the potency of the inhibitors in blocking GlcCer synthase was mainly dependent upon hydrophobic and electronic properties of the substituent. Surprisingly, a linear relationship was found between log [IC$_{50}$] and hydrophobic parameter ($\pi$)+electronic parameter ($\delta$). This correlation suggested that electron donating and hydrophilic characters of the substituent enhance the potency as an inhibitor. This observation resulted in the synthesis of novel compounds that are more active in blocking glucosylceramide formation. Two compounds, dioxy D-t-P4 compounds, D-t-3',4'-ethylenedioxy-P4 and D-t-4'-hydroxy-P4, were observed to be significantly more potent than other tested inhibitors. In particular, at 11.3 nM D-t-3',4'-ethylenedioxy-P4, 80% of glucosylceramide in MDCK cell was depleted without any ceramide accumulation and cell growth inhibition. The potency of D-t-3',4'-ethylenedioxy-P4 appears to be not only regulated by hydrophobic and electronic properties but also by stearic properties of the substituents on the phenyl group.

Materials and Methods

Materials. The acetophenones and amines were from Aldrich Chemical Co., St. Louis, Mo., Lancaster Synthesis Inc., Windham, N.H. and Maybridge Chemical Co., Cornwall, UK. Silica gel for column chromatography (70–230 mesh ASTM) and Silica gel thin layer chromatography plates were purchased from Merck Co. The reagents and their sources were: non-hydroxy fatty acid ceramide from bovine brain and delipidated bovine serum albumin (BSA) from Sigma; dioleoyphosphatidylcholine from Avanti; DL-dithiothreitol from Calbiochem; 1-[$^3$H]-glucose uridine diphosphate from NEN. Octanoylsphingosine, glucosylceramide and sodium sulfatide were prepared as previously described. Abe, A. et al., *Eur. J. Biochemistry* 210:765–773 (1992).

General synthesis of inhibitors. The aromatic inhibitors were synthesized by the Mannich reaction from 2-N-acylaminoacetophenone, paraformaldehyde, and pyrrolidine, and then the reduction from sodium borohydride as described before. Inokuchi, J. et al., *J. Lipid. Res.* 28:565–571 (1987); Abe, A. et al., *J. Lipid. Res.* 36:611–621 (1995). The reaction produces a mixture of four isomers, due to the presence of two asymmetric centers. For these syntheses in which phenyl-substituted starting materials were used, the chloro, methoxy, methylenedioxy, methyl groups in the acetophenone structure were brominated and converted to the primary amine. Bromation of the methoxyacetophenone, dimethyoxyacetophenone, 3',4'-(methylenedioxy)acetophenone were performed in chloroform at room temperature and recrystallized from ethyl acetate and hexane.

Synthesis of 1-(4'-hydroxy)phenyl-2-palmitoylamino-3-pyrrolidino-1-propanol.

Figure 8:
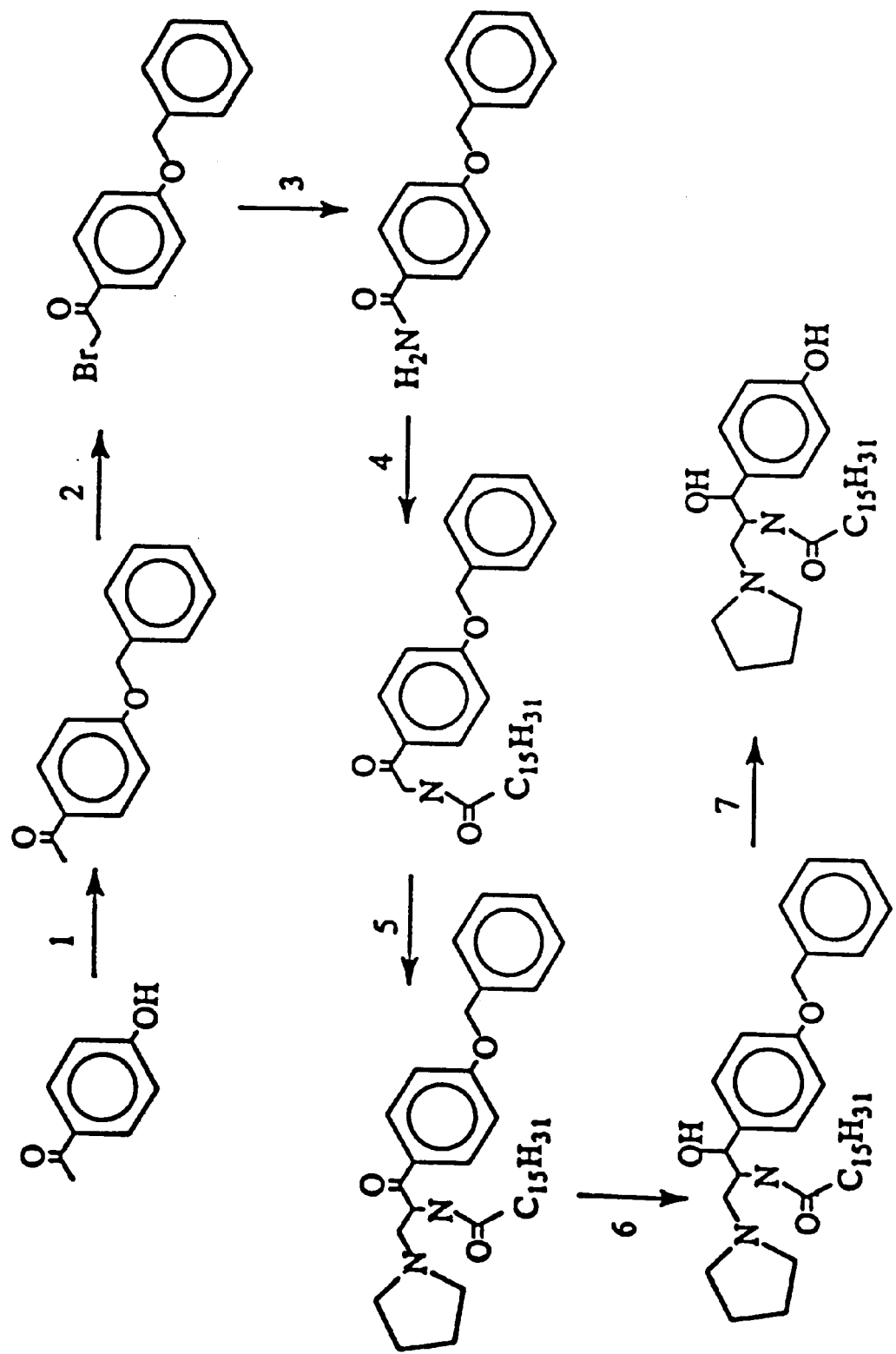
FIG. 8 is a schematic of the synthetic pathway for 4'-hydroxy-1-phenyl-2-palmitoylamino-3-pyrrolidino-1-propanol.

The synthesis of 1-(4'-hydroxy)phenyl-2-palmitoylamino-3-pyrrolidino-1-propanol is described in detail in FIG. 8. This synthesis differs from those of the other compounds because of the need for the placement of a protecting group on the free hydroxyl (step 1) and its subsequent removal (step 7). All other syntheses employ a similar synthetic scheme (steps 2 to 6).

4'-Benzyloxyacetophenone formation (step 1)

4'-Hydroxyacetophenone (13.62 g, 100 mmol), benzylbromide (17.1 g, 100 mmol), and cesium carbonate (35.83 g, 100 mmol) were added to tetrahydrofuran at room temperature and stirred overnight. The product was concentrated to dryness and recrystallized from ether and hexane to yield 15 g of 4'-benzyloxyacetophenone which appeared as a white powder. An R$_f$ of 0.42 was observed when resolved by thin layer chromatography using methylene chloride. $^1$H nmr ($\delta$, ppm, CDCl$_3$), 7.94 (2H, $\delta$, 8.8 Hz, O—Ar—C(O)), 7.42 (5H, m, Ar'CH$_2$O—), 7.01 (2H, $\delta$, 8.8 Hz, O—Ar—C(O)), 5.14 (2H, s, Ar'CH$_2$O—), 2.56 (3H, S, CH$_3$).

Bromination of 4'-benzyloxyacetophenone (step 2)

Bromine (80 mmol) was added dropwise over 5 min to a stirred solution of 4'-benzyloxyacetophenone (70 mmol) in 40 ml chloroform. This mixture was stirred for an additional 5 min and quenched with saturated sodium bicarbonate in water until the pH reached 7. The organic layers were combined, dried over MgSO$_4$, and concentrated to dryness. The crude mixture was purified over a silica gel column and eluted with methylene chloride to yield 2-bromo-4'-benyloxyacetophenone. An R$_f$ of 0.62 was observed when resolved by thin layer chromatography using methylene chloride. 1H nmr ($\delta$, ppm, CDCl$_3$), 7.97 (2H, $\delta$, 9.2 Hz, O—Ar—C(O)), 7.43 (5H, m, Ar'CH$_2$O—), 7.04 (2H, $\delta$, 9.0 Hz, O—Ar—C(O)), 5.15 (2H, s, Ar'CH$_2$O—), 4.40 (2H, s, CH$_2$Br).

2-Amino-4'-benzyloxyacetophenone HCl formation (step 3)

Hexamethylenetetramine (methenamine, 3.8 g, 23 mmol) was added to a stirred solution of 2-bromine-4'- benyloxyacetophenone (6.8 g, 23 mmol) in 100 ml chloroform. After 4 h the crystalline adduct was filtered and washed with chloroform. The product was dried and heated with 150 ml methanol and 8 ml of concentrated HCl in an oil bath at 85° C. for 3 h. Upon cooling the precipitated hydrochloride salt (2.5 g) was removed by filtration. The filtrate was left at −20° C. overnight and additional product (2.1 g) was isolated. The yield was 4.6 g (82.6%). [M$^+$H]$^+$: 242 for $C_{15}H_{16}NO_2$. $^1$H nmr ($\delta$, ppm, $CDCl_3$), 8.38 (2H, bs, $NH_2$), 7.97 (2H, $\delta$, 8.8 Hz, O—Ar—C(O)), 7.41 (5H, m, Ar'CH2O—), 7.15 (2H, $\delta$, 8.6 Hz, O—Ar—C(O)), 5.23 (2H, s, Ar'CH$_2$O—), 4.49 (2H, s, CH$_2$NH$_2$).

2-Palmitoylamino-4'-benyloxyacetophenone formation (step 4)

Sodium acetate (50% in water, 29 ml) was added in three portions to a stirred solution of 2-amino-4'-benzyloxyacetophenone HCl (4.6 g, 17 mmol) and tetrahydrofuran (200 ml). Palmitoyl chloride (19 mmol) in tetrahydrofuran (25 ml) was added dropwise over 20 min yielding a dark brown solution. The mixture was stirred overnight at room temperature. The aqueous fraction was removed by use of a separatory funnel and chloroform/methanol (2/1, 150 ml) was added to the organic layer which was then washed with water (50 ml). The yellow aqueous layer was extracted once with chloroform (50 ml). The organic solutions were then pooled and rotoevaporated until near dryness. The residue was redissolved in chloroform (100 ml) and crystallized by the addition of hexane (400 ml). The flask was cooled to 4° C. for 2 h. The crystals were filtered and washed with cold hexane and dried in a fume hood overnight. The product yield was 3.79 g (8 mmol). An R$_f$ of 0.21 was observed when resolved by thin layer chromatography using methylene chloride. [M$^+$H]$^+$: 479 for $C_{31}H_{45}NO_3$. $^1$H nmr ($\delta$, ppm, $CDCl_3$), 7.96 (2H, $\delta$, 8.8 Hz, O—Ar—C(O)), 7.40 (5H, m, Ar'CH$_2$O—), 7.03 (2H, $\delta$, 8.8 Hz, O—Ar—C(O)), 6.57 (1H, bs, NH$_2$), 5.14 (2H, s, Ar'CH$_2$O—), 4.71 (2H, s, C(O)CH$_2$NHC(O)), 2.29 (2H, t, 7.4 Hz, C(O)CH$_2$(CH$_2$)$_{13}$CH$_3$), 1.67 (2H, m, C(O)CH$_2$ (CH$_2$)$_{13}$CH$_3$), 0.87 (3H, t, 6.7 Hz, C(O)CH$_2$(CH$_2$)$_{13}$CH$_3$).

1-(4'-Benzyloxy)phenyl-2-palmitoylamino-3-pyrrolidino-1-propanol formation (steps 5 and 6)

2-Palmitoylamino-4'-benyloxyacetophenone (3.79 g, 8.0 mmol), paraformaldehyde (0.25 g, 2.7 mmol), pyrrolidine (0.96 ml, 11.4 mmol) and ethanol (70 ml) were stirred under nitrogen. Concentrated HCl (0.26 ml) was added through the condensor and the mixture was heated to reflux for 16 h. The resultant brown solution was cooled on ice and then sodium borohydride (1.3 g, 34 mmol) was added in three portions. The mixture was stirred at room temperature overnight, and the product was dried in a solvent evaporator. The residue was redissolved in dichloromethane (130 ml) and hydrolyzed with 3N HCl (pH~4). The aqueous layer was extracted twice with dichloromethane (50 ml). The organic layers were pooled and washed twice with water (30 ml), twice with saturated sodium chloride (30 ml), and dried over anhydrous magnesium sulfate. The dichloromethane solution was rotoevaporated to a semisolid and purified by use of a silica rotor using a solvent consisting of 10% methanol in dichloromethane. This yielded a mixture of DL-threo- and DL-etythro enantiomers (2.53 g, 4.2 mmol). An R$_f$ of 0.43 for the erythro diastereomers and 0.36 for the threo diastereomers was observed when resolved by thin layer chromatography using methanol:methylene chloride (1:9). [M$^+$H]$^+$: 565 for $C_{36}H_{56}N_2O_3$.

1-(4'-Hydroxy)phenyl-2-palmitoylamino-3-pyrrolidino-1-propanol formation (step 7)

A suspension of 20% Pd/C (40 mg) in acetic acid (15 ml) was stirred at room temperature under a hydrogen balloon for 15 min. 1-(4'-Benzyloxy)phenyl-2-hexadecanoylamino-3-pyrrolidino-1-propanol (420 mg, 0.74 mmol) was added and the solution was stirred overnight. The suspension was filtered through a glass frit, and the filter was rinsed with acetic acid:methylene chloride (1:1, 5 ml). The filtrate was concentrated in vacuo and crystallized to yield a pale yellow semisolid (190 mg, 0.4 mmol). An R$_f$ of 0.21 was observed when resolved by thin layer chromatography using methanol:methylene chloride (1:9). [M$^+$H]$^+$: 475 for $C_{29}H_{50}N_2O_3$. $^1$H nmr ($\delta$, ppm, $CDCl_3$), 7.13 (4H, m, ArCHOH—), 7.14 (1H, $\delta$, 6.9 Hz, —NH—), 5.03 (1H, $\delta$, 3.3 Hz, CHOH—), 4.43 (1 H, m, c-(CH$_2$CH$_2$)$_2$NCH$_2$CH), 3.76 (2H, m, c-(CH$_2$CH$_2$)$_2$N—), 3.51 (1H, m, c-(CH$_2$CH$_2$)$_2$NCH$_2$—), 3.29 (1 H, m, c-(CH$_2$CH$_2$)$_2$NCH$_2$—), 2.97 (3H, m, c-(CH$_2$CH$_2$)$_2$N— and ArC(OH)H—), 2.08 (6H, m, —C(O) CH$_2$(CH$_2$)$_{13}$CH$_3$ and c-(CH$_2$CH$_2$)$_2$N—, 1.40 (2H, m, C(O) CH$_2$CH$_2$(CH$_2$)$_{12}$CH$_3$), 1.25 (2H, m, —C(O)CH$_2$CH$_2$(CH$_2$)$_{12}$CH$_3$), 0.87 (3H, t, 6.7 Hz, C(O)CH$_2$(CH$_2$)$_{13}$CH$_3$).

Synthesis of D-threo-1-(3',4'-ethylenedioxy)phenyl-2-palmitoylamino-3-pyrrolidino-1-propanol 2-Amino-3',4'-(ethylenedioxy)acetophenone HCl Hexamethylenetetramine (methenamine, 5.4 g, 0.039 mol) was added to a stirred solution of phenacylbromide (10.0 g, 0.039 mol) in 200 ml chloroform. After 2 h, the crystalline adduct was filtered and washed with chloroform. The product was then dried and heated with methanol (200 ml) and concentrated HCl (14 ml) in an oil bath at 85° C. for 2 h. On cooling, the precipitated ammonium chloride was removed by filtration and the filtrate was left in a freezer overnight. After filtration the crystallized phenacylamine HCl was washed with cold isopropanol and then with ether. The yield of this product was ~7.1 g (81%).

2-Palmitoylamino-3',4'-(ethylenedioxy)acetophenone

Aminoacetophenone HCl (7.1 g, 31 mmol) and tetrahydrofuran (300 ml) were placed in a 1 liter three-neck round bottom flask with a large stir bar. Sodium acetate (50% in water, 31 ml) was added in three portions to this suspension. Palmitoyl chloride (31 ml, 10% excess, 0.036 mol) in tetrahydrofuran (25 ml) was then added dropwise over 20 min to yield a dark brown solution. This mixture was then stirred for an additional 2 h at room temperature. The resultant mixture was poured into a separatory funnel to remove the aqueous solution. Chloroform/methanol (2/1, 150 ml) was then added to the organic layer and washed with water (50 ml). The yellow aqueous layer was extracted once with chloroform (50 ml). The organic solutions were pooled and rotoevaportated until almost dry. The residue was redissolved in chloroform (100 ml) and crystallized by the addition of hexane (400 ml). The flask was then cooled to 4° C. for 2 h. The crystals were filtered and washed with cold hexane until they were almost white and then dried in a fume hood overnight. The yield of the product was 27 mmol (11.6 g).

D-threo-1-(3',4'-ethylenedioxy)phenyl-2-palmitoylamino-3-pyrrolidino-1-propanol

Almitoylaminoacetophenone (11.6 g, 0.027 mol), paraformaldehyde (0.81 g, 0.009 mol), pyrrolidine (3.6 ml, 0.042 mol) and ethanol (250 ml) were added to a 500 ml round flask under nitrogen flow. Concentrated HCl (0.8 ml) was added to this mixture through the reflux condenser and the mixture was refluxed for 16 h. The brown solution was cooled in an ice-bath. Sodium borohydride (2.28 g, 0.06 mol) was added in three portions. This mixture was stirred at room temperature for 3 h and then rotoevaporated. The residue was dissolved in 130 ml of dichloromethane and the borate complex hydrolyzed with HCl (3N) until the pH was approximately 4. The aqueous layer was extracted twice with 50 ml dichloromethane. The organic layers were pooled and washed twice with $H_2O$ (30 ml), saturated NaCl (30 ml) and dried over anhydrous $MgSO_4$. The dichloromethane solution was rotoevaporated to a viscous oil which was purified by use of a Chromatotron with a solvent consisting of 10% methanol in dichloromethane to obtain a mixture of DL-threo and erythro enantiomers (2.24 g, 0.004 mol).

Resolution of inhibitor enantiomers. High performance liquid chromatography (HPLC) resolution of the enantiomers of DL-threo and DL-erythro are performed using a preparative HPLC column (Chirex 3014: [(S)-val-(R)-1-(a-naphtyl)ethylamine, 20×250 mm: Phenomenex], eluted with hexane-1,2-dichloroethane-ethanol-trifluroacetic acid 64:30:5.74:0.26, at a flow rate of 8 ml/min. The column eluent was monitored at 254 nm in both the preparative and analytical modes. Isolated products were reinjected until pure by analytical HPLC analysis, determined using an analytical Chirex 3014 column (4.6×250 mm) and the above solvent mixture at flow rate of 1 ml/min.

Glycosylceramide synthase activity. The enzyme activity was measured by the method previously described in Skukla, G. et al., *Biochim. Biophys. Acta* 1083:101–108 (1991). MDCK cell homogenate (120 µg of protein) was incubated with uridinediphosphate [$^3$H]glucose (100,000 cpm) and liposomes consisting of 85 µg octanoylsphingosine, 570 µg dioleoyphosphatidylcholine and 100 µg sodium sulfatide in 200 µl of reaction mixture and kept for 1 h at 37° C. P4 and P4 derivatives dissolved in dimethyl sulfoxide were dispersed into the reaction mixture after adding liposomes. The final concentration of dimethyl sulfoxide was kept 1% under which the enzyme activity was not at all inhibited.

Cell culture and lipid extraction. One half million of MDCK cells were seeded into 10 cm style dish containing 8 ml serum free DMEM supplemented medium. Shayman, J. A. et al., *J. Biol. Chem.* 265:12135–12138 (1990). After 24 h the medium was replaced with 8 ml of the medium containing 0, 11.8, 118 or 1180 nM D-t-P4, D-t-3',4'-ethylenedioxy-P4 or D-4'-hydroxy)-P4. The GlcCer synthase inhibitors were added into the medium as a one to one complex with delipidated BSA. Abe, A. et al., *J. Lipid. Res.* 36:611–621 (1995); Abe, A. et al., *Biochim. Biophys. Acta* 1299:331–341 (1996). The cells were incubated for 24 h or 48 h with the inhibitors. After the incubation, the cells were washed twice with 8 ml of cold PBS and fixed with 2 ml of cold methanol. The fixed cells were scraped and transferred to a glass tube. Another one ml of methanol was used to recover the remaining cells in the dish.

Three ml of chloroform was added to the tube and briefly sonicated using a water bath type sonicator. After centrifugation at 800 g for 5 min, the supernatant was transferred into another glass tube. The residues were reextracted with chloroform/methanol (1/1). After the centrifugation, the resultant supernatant was combined with the first one. The residues were air-dried and kept for protein analysis. Adding 0.9% NaCl to the supernatant combined, the ratio of chloroform/methanol/aqueous was adjusted to 1/1/1. After centrifugation 800 g for 5 min, the upper layer was discarded. Methanol/water (1/1) with the same amount of volume of the lower layer was used to wash. The resultant lower layer was transferred into a small glass tube and dried down under a stream of nitrogen gas. A part of the lipid was used for lipid phosphate determination. Ames, B. N., *Methods Enzymol.* 8:115–118 (1966). The remainder was analyzed using HPTLC (Merck).

Results

Synthesis of P4 and P4 derivatives. The preparation of P4 derivatives utilized the Mannich reaction from 2-N-acylaminoacetophenone, paraformaldehyde, and pyrrolidine, and then the reduction of DL-pyrrodino ketone from sodium borohydride. In most cases, no isolation of DL-pyrrodino ketones were performed to maintain solubility. The overall yields of the DL-threo and DL-erythro syntheses were ~10–30%. These derivatives were purified by the either silica gel column or rotors with solvent 5–12% methanol in dichloromethane to optimize the separation from the chiral column. To obtain the best separation, each injection contains no more than 150 mg, and fractions were pooled to obtain sufficient quantity of isomer of D-threo for further biological characterization.

Figure 4A:
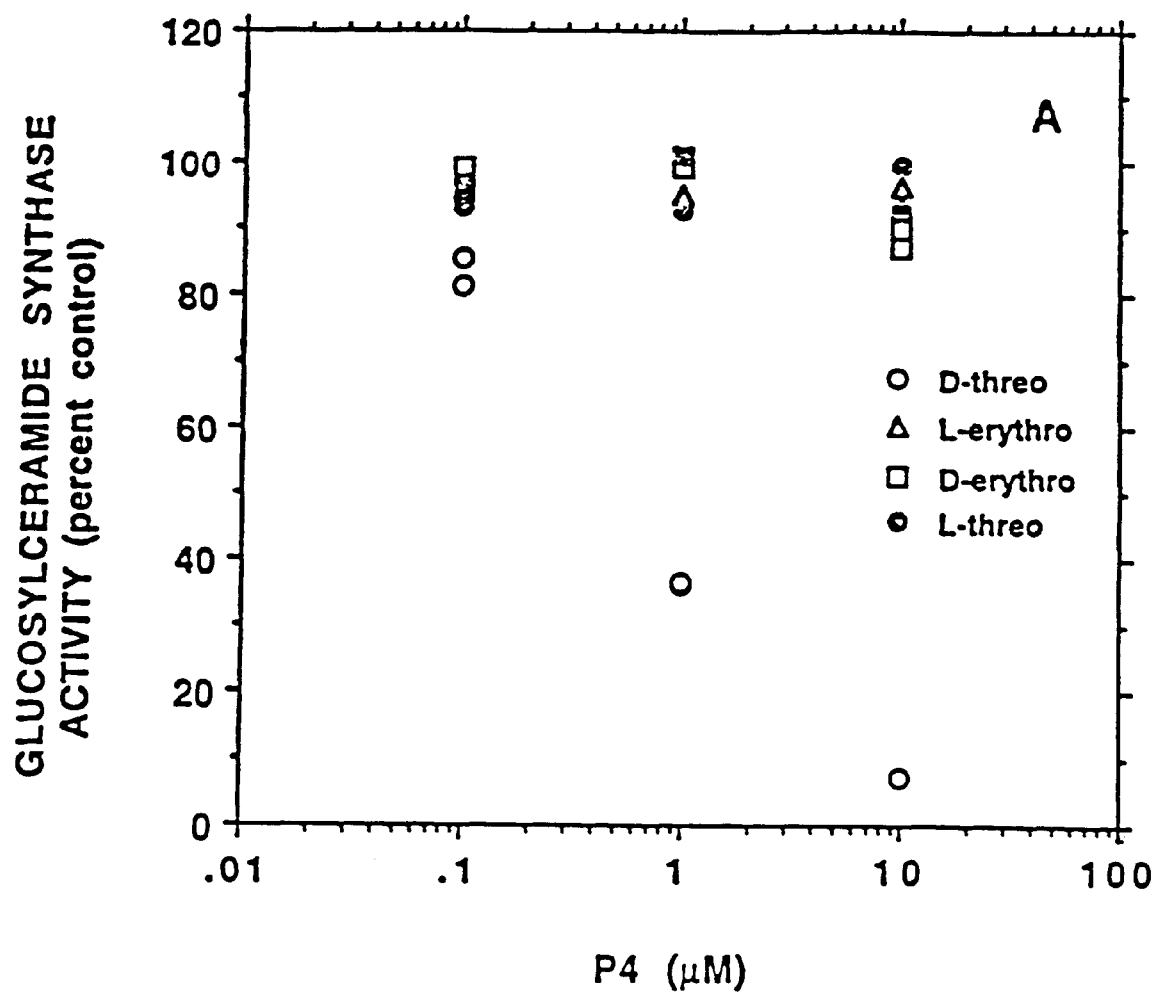
FIGS. 4A and 4B are graphs showing the effects of P4 and p-methoxy-P4 on GlcCer synthase activity.
Figure 9:
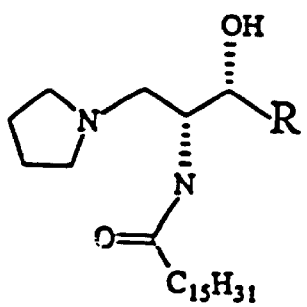
FIG. 9 is an illustration of the structures of P4 and of phenyl-substituted P4 homologues.
Figure 9:
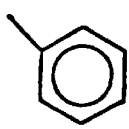
Figure 9:
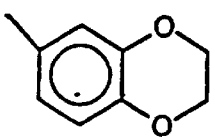
Figure 9:
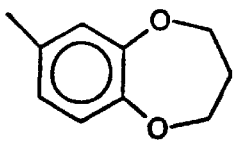
Figure 9:
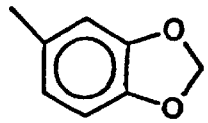
Figure 9:
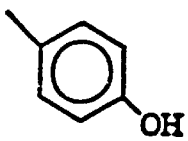
Figure 10:
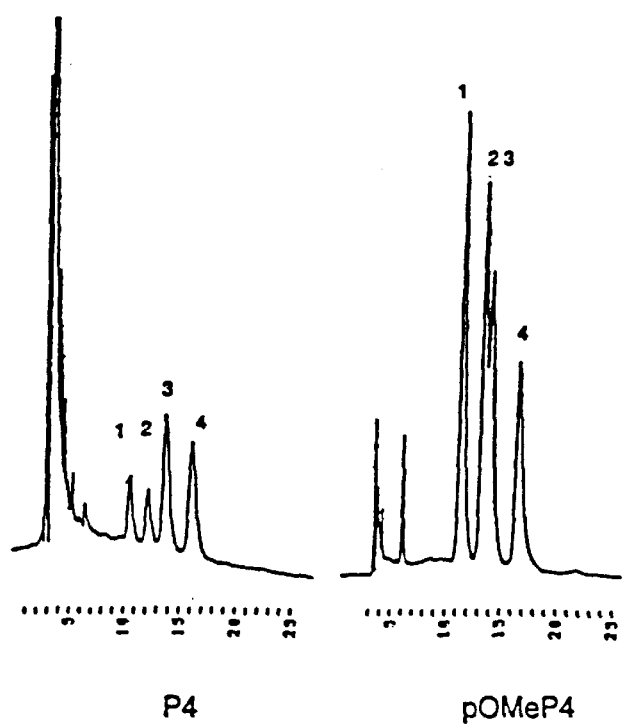
FIG. 10 is an HPLC chromatogram showing the separation of the enantiomers of P4 and p-methoxy-P4 by chiral chromatography.

Resolution of PDMP homologues by chiral chromatography. The structures of the parent compound, D-threo-P4 and the phenyl-substituted homologues including the new dioxy-substituted and 4'-hydroxy-P4 homologues are shown in FIG. 9. Initially the effect of each P4 isomer separated by chiral chromatography on GlcCer synthase activity was determined (FIG. 10). Four peaks were observed for the chiral separation of P4. Peaks 1 and 2 represented the erythro diastereomers and 3 and 4 represented the threo diastereomers as determined by a sequential separation of the P4 mixture by reverse phase chromatography followed by the chiral separation. The enzyme activity was specifically inhibited by the fourth peak, the D-threo isomer (FIG. 4A). This specificity for the D-threo enantiomer was consistent with the previous results observed in PDMP and PDMP homologues (2–4). The $IC_{50}$ of D-threo-P4 was 0.5 mM for GlcCer synthase activity measured in the MDCK cell homogenates.

Figure 4B:
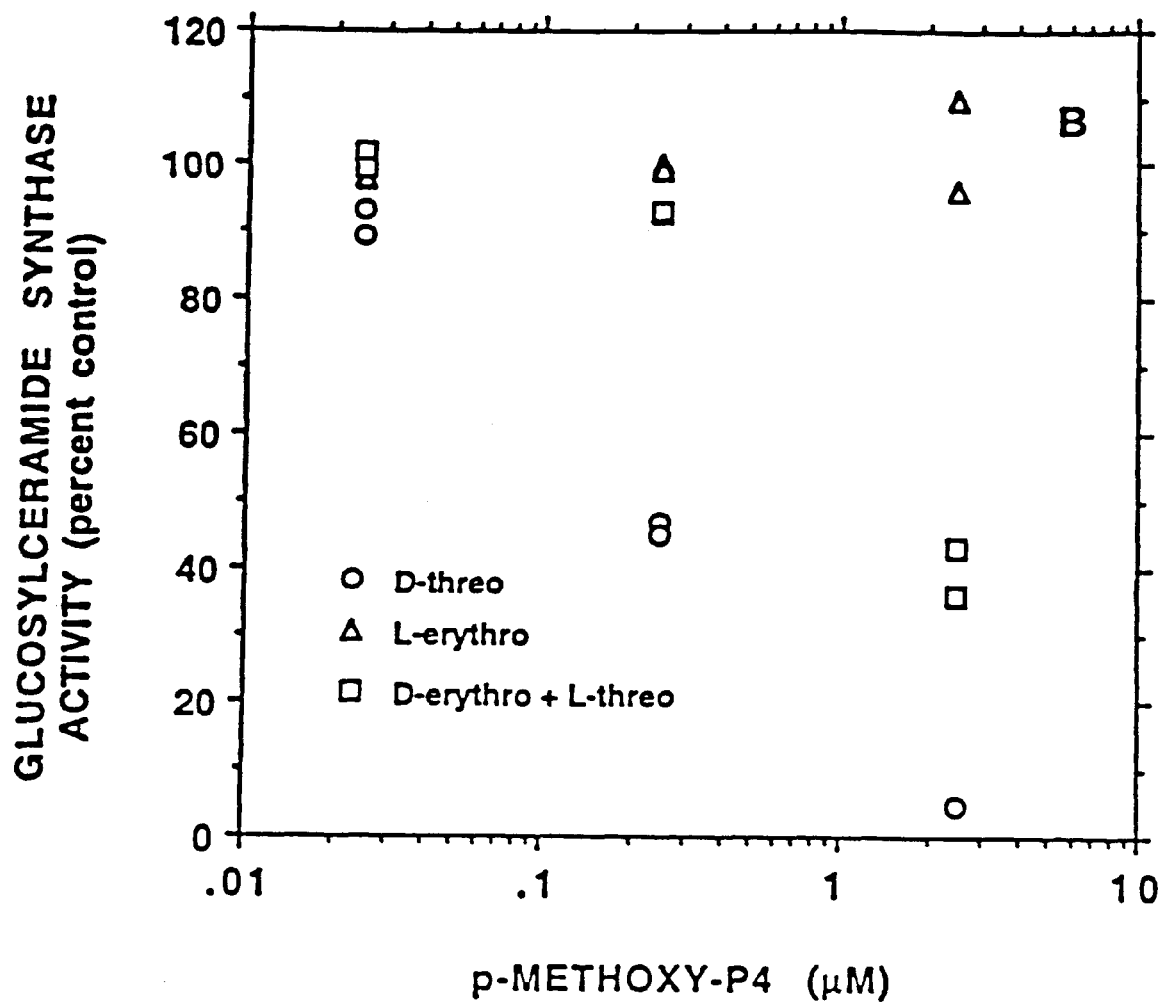

Effects of P4 and P4 Derivatives with a Single Substituent of Phenyl Group on GlcCer Synthase Activity The effect of each P4 isomer on GlcCer synthase activity was analyzed. The reaction was carried out in the absence or presence of 0.1, 1.0 or 10 µM P4 (FIG. 4A) or p-methoxy-P4 (FIG. 4B). As shown in FIG. 4A, the enzyme activity was specifically inhibited by D-threo isomer. In FIG. 4A, the symbols are denoted as follows: D-threo (•), D-erythro (□), L-threo and (·), L-erythro (Δ). This specificity is consistent with previous results observed in PDMP and PDMP homologs. Inokuchi, J. et al., *J. Lipid. Res.* 28:565–571 (1987); Abe, A. et al., *J. Lipid. Res.* 36:611–621 (1995). The $IC_{50}$ of D-t-P4 was 500 nM.

As set forth herein, the addition of a p-methoxy group to DL-t-P4 was found to enhance the effect of the inhibitor on the enzyme activity. Abe, A. et al., *J. Lipid. Res.* 36:611–621 (1995). As shown in FIG. 4B, it was confirmed that the enzyme activity was potently inhibited by D-threo-p-methoxy-P4 whose $IC_{50}$ was 200 nM. In FIG. 4B, □ denotes a mixture of D-erythro and L-threo isomers contaminated with a small amount of the D-threo isomer. Chiral chromatography of the four p-methoxy-P4 enantiomers failed to completely resolve to baseline each enantiomer (FIG. 10). A slight inhibition of the enzyme activity by p-methyoxy-P4 in a combined D-erythro and L-threo mixture (peaks 2 and 3, FIG. 10) was observed; this was due to contamination of the D-threo isomer (peak 4, FIG. 10) into these fractions.

A series of D-t-P4 derivatives containing a single substituent on the phenyl group were investigated. As shown in Table 8, the potency of the derivatives as inhibitors were inferior to that of D-t-P4 or p-methoxy-D-t-P4. In many drugs, the influence of an aromatic substituent on the biological activity has been known and predicted. Högberg, T. et al., Theoretical and experimental methods in drug design applied on antipsychotic dopamine antagonists. Larsen, P. K., and Bundgaard, H., "Textbook of Drug Design and Development," pp. 55–91 (1991). Generally $IC_{50}$ is described as the following equation:

$$\log(1/IC_{50}) = a(\text{hydrophobic parameter }(\pi)) + b(\text{electronic parameter }(\sigma)) + c(\text{stearic parameter}) + d(\text{other descriptor}) + e$$

where a, b, c, d and e are the regression coefficients. Högberg, T. et al., Theoretical and experimental methods in drug design applied on antipsychotic dopamine antagonists. Larsen, P. K., and Bundgaard, H., "Textbook of Drug Design and Development," pp. 55–91 (1991).

The hydrophobic effect, $\pi$, is described by the equation $\pi = \log P_X - \log P_H$ where $P_X$ is the partition coefficient of the substituted derivative and $P_H$ is that of the parent compound, measured as the distribution between octanol and water.

The electronic substituent parameter, $\sigma$, was originally developed by Hammett (Hammett, L. P., In Physical Organic Chemistry, McGraw-Hill, New York (1940)) and is expressed as $\sigma = \log K_X - \log K_H$, where $K_X$ and $K_H$ are the ionization constants for a para or meta substituted derivative and benzoic acid respectively. Positive $\sigma$ values represent electron withdrawing properties and negative $\sigma$ values represent electron donating properties.

Figure 5:
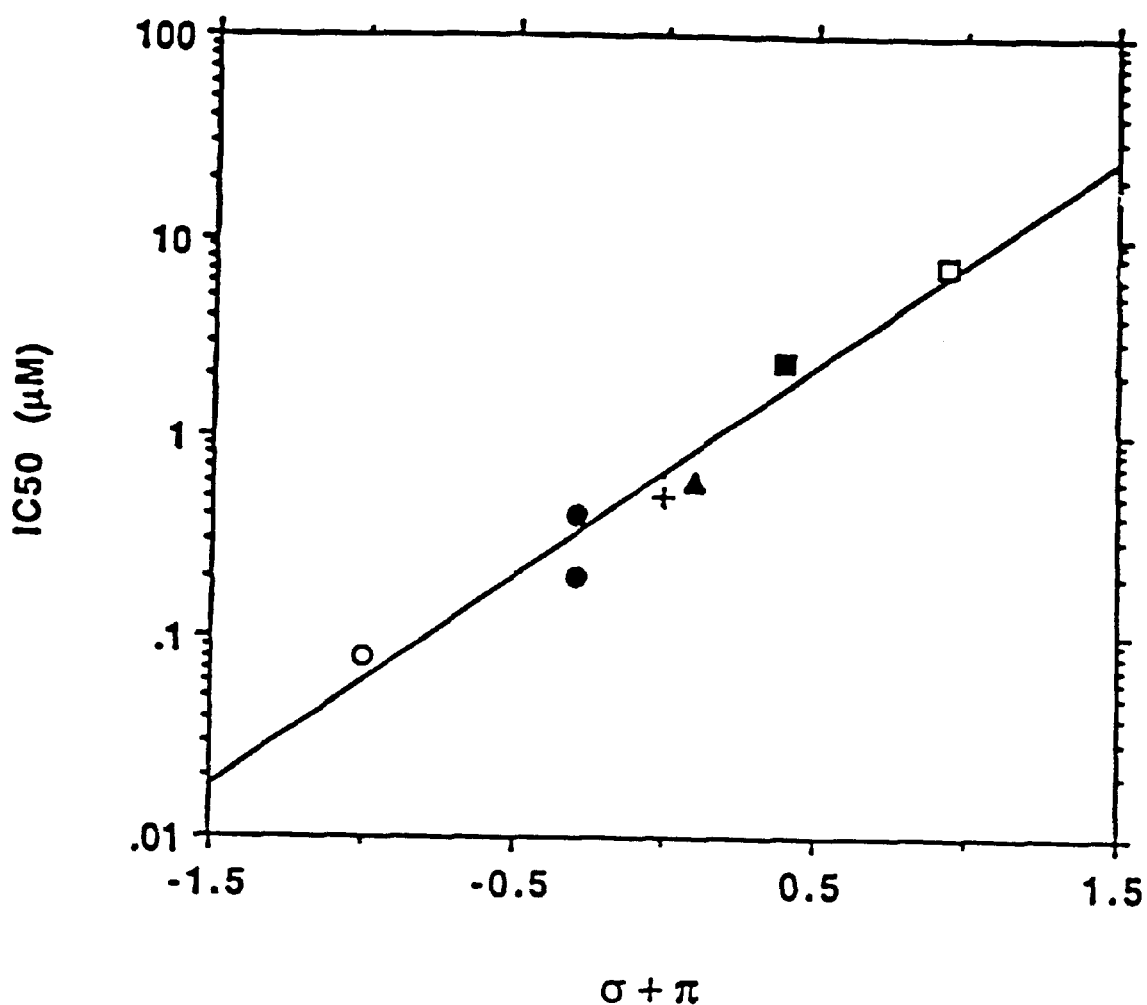
FIG. 5 is a graph showing the linear relationship between the inhibition of GlcCer synthase activity and electronic parameter (δ) and hydrophobic parameter (π)

The potency of D-threo-P4 and P4 derivatives as an inhibitor is mainly dependent upon two factors, hydrophobic and electronic properties, of a substituent of phenyl group (Table 8). Surprisingly, a linear relationship was observed between log ($IC_{50}$) and $\pi+\sigma$ (FIG. 5). These findings suggest that the more negative the value of $\pi+\sigma$, the more potent is D-threo-P4 derivatives made as GlcCer synthase inhibitor.

The data in Table 8 indicate that the potency of D-t-P4 and P4 derivatives as an inhibitor is mainly dependent upon two properties, hydrophobic and electronic properties, of a substituent of the phenyl group. Surprisingly, a linear relationship was observed between $\log(IC_{50})$ and $\pi+\sigma$ (FIG. 5). These findings suggest that the more negative the value of $\pi+\sigma$, the more potent the D-t-P4 derivative as a GlcCer synthase inhibitor.

TABLE 8

| D-threo-P4 derivative | $\sigma + \pi^*$ | $IC_{50}$ ($\mu$M)** |
|---|---|---|
| p-methoxy | −0.29 | 0.2 |
| P-4 | 0.00 | 0.5 |
| m-methoxy-P4 | 0.10 | 0.6 |

TABLE 8-continued

| D-threo-P4 derivative | $\sigma + \pi^*$ | $IC_{50}$ ($\mu$M)** |
|---|---|---|
| p-methyl-P4 | 0.39 | 2.3 |
| p-chloro-P4 | 0.94 | 7.2 |

*These values were estimated from the Table in Högberg, T. et al., Theoretical and experimental methods in drug design applied on antipsychotic dopamine antagonists. Larsen, P. K., and Bundgaard, H., "Textbook of Drug Design and Development," pp. 55–91 (1991), for methoxy, $\sigma_m = 0.12$, $\sigma_p = -0.27$, $\pi = -0.02$; hydro, $\sigma = 0$, $\pi = 0$; methyl, $\sigma_p = -0.17$, $\pi = 0.56$; chloro, $\sigma_p = 0.23$, $\pi = 0.71$.
**These values were derived from FIGS. 4A and 4B. For other compounds the same analytical approach as shown in FIGS. 4A and 4B was carried out to obtain the $IC_{50}$.

Figure 11:
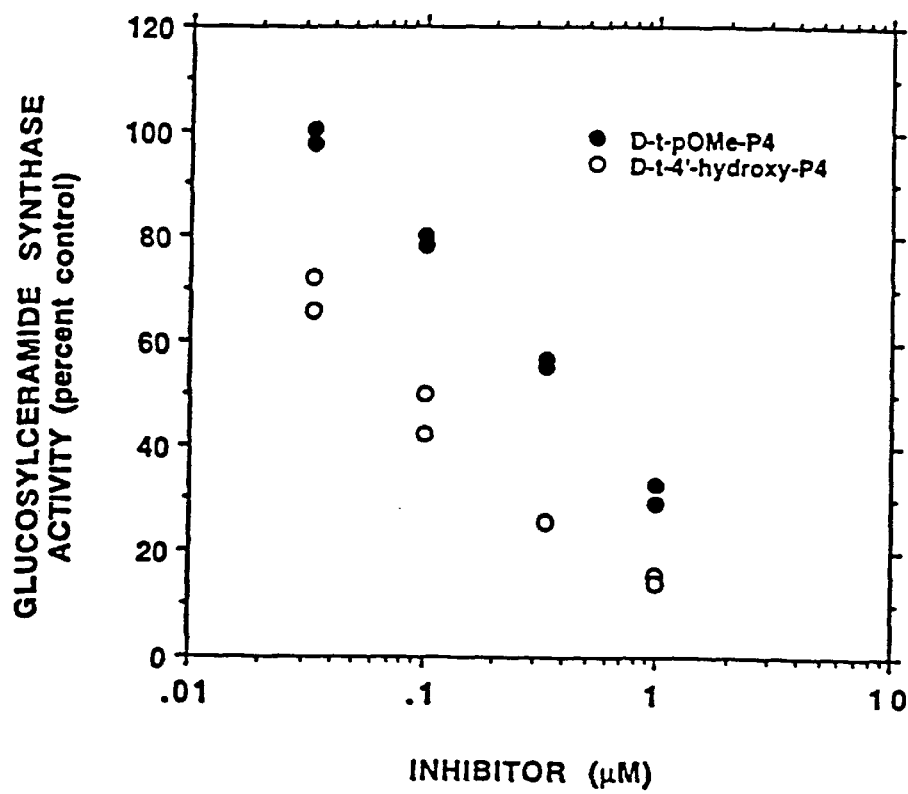
FIG. 11 is a graph showing the effects of D-threo-4'-hydroxy-P4 as compared to D-threo-p-methoxy-P4 on GlcCer synthase activity.

The p-hydroxy-substituted homologue was a significantly better GlcCer synthase inhibitor. The strong association between $\pi+\sigma$ and GlcCer synthase inhibition suggested that a still more potent inhibitor could be produced by increasing the electron donating and decreasing the lipophilic properties of the phenyl group substituent. A predictably negative $\pi+\sigma$ value would be observed for the p-hydroxy homologue. This compound was synthesized and the D-threo enantiomer isolated by chiral chromatography. An $IC_{50}$ of 90 nM for GlcCer synthase inhibition was observed (FIG. 11), suggesting that the p-hydroxy homologue was twice as active as the p-methoxy compound. Moreover, the linear relationship between the log (IC50) and $\pi+\sigma$ was preserved (open circle, FIG. 4).

Effects of 3',4'-dioxy-D-threo-P4 Derivatives on GlcCer Synthase Activity

The result in FIG. 5 suggested that an electron donating and hydrophilic substituent of phenyl group makes the GlcCer synthase inhibitor potent. To attain further improvement of the inhibitor, another series of P4 derivatives with methylenedioxy, ethylenedioxy and trimethyidioxy substitutions on the phenyl group were designed (FIG. 9).

Figure 6:
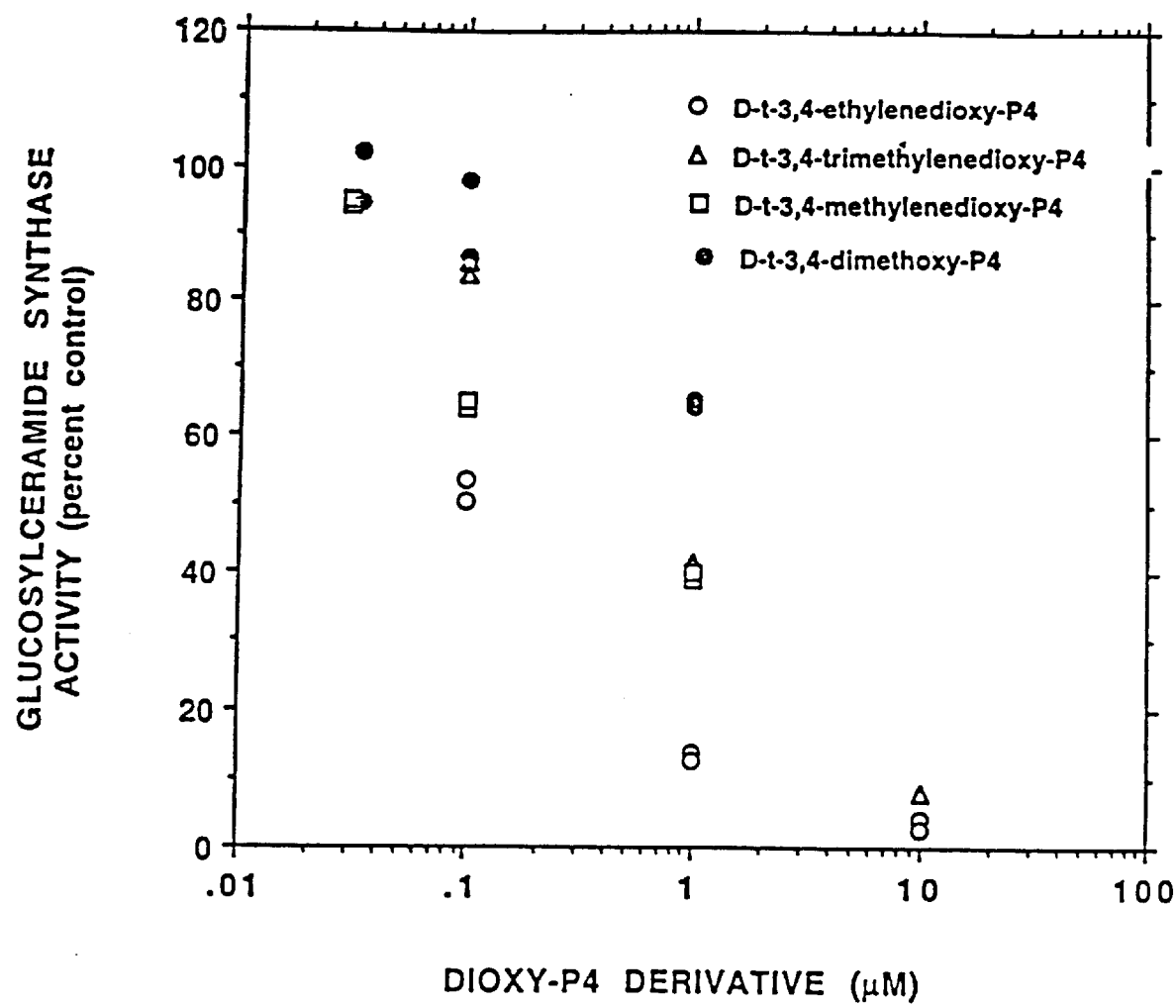
FIG. 6 is a graph showing the effects of dioxy P4 derivatives on GlcCer synthase activity.

As shown in FIG. 6, the enzyme activity was markedly inhibited by D-t-3',4'-ethylenedioxy-P4 whose $IC_{50}$ was 100 nM. In FIG. 6, □ denotes D-t-3',4'-methylenedioxy-P4, o denotes D-t-3',4'-ethylenedioxy-P4, Δ denotes D-t-3',4'-trimethylenedioxy-P4 and•denotes D-t-3',4'-dimethyoxy-P4. One the other hand, the $IC_{50}$s for D-t-3',4'-methylenedioxy-P4 and D-t-3',4'-trimethylenedioxy-P4 were about 500 and 600 nM, respectively. These results suggest that the potency of D-t-3',4'-ethylenedioxy-P4 is not only regulated by hydrophobic and electronic properties but also by other factors, most likely stearic properties, induced from the dioxy ring on the phenyl group.

Interestingly, D-t-3',4'-dimethoxy-P4 was inferior to these dioxy derivatives, even to D-t-P4 or m- or D-t-p-methoxy-P4, as an inhibitor (FIG. 6). As the parameters, $\sigma_m$, $\sigma_p$ and $\pi$, for methoxy substituent are 0.12, −0.27 and −0.02, respectively (Högberg, T. et al., Theoretical and experimental methods in drug design applied on antipsychotic dopamine antagonists. Larsen, P. K., and Bundgaard, H., "Textbook of Drug Design and Development," pp. 55–91 (1991)), the value of $\pi+\sigma$ of D-t-dimethoxy P4 is presumed to be negative. Therefore the dimethoxy-P4 is thought to deviate quite far from the correlation as observed in FIG. 5. There may be a repulsion between two methoxy groups in the dimethoxy-P4 molecule that induces a stearic effect that was negligible in mono substituent D-t-P4 derivatives studied in FIG. 5. GlcCer synthase is thought to possess a domain that interacts with D-t-PDMP and PDMP homologs and that modulates the enzyme activity. Inokuchi, J. et al., *J. Lipid.*

Res. 28:565–571 (1987); Abe, A. et al., *Biochim. Biophys. Acta* 1299:331–341 (1996). The stearic effect generated by an additional methoxy group may affect the interaction between the enzyme and the inhibitor. As a result, the potency as an inhibitor is markedly changed.

Figure 12:
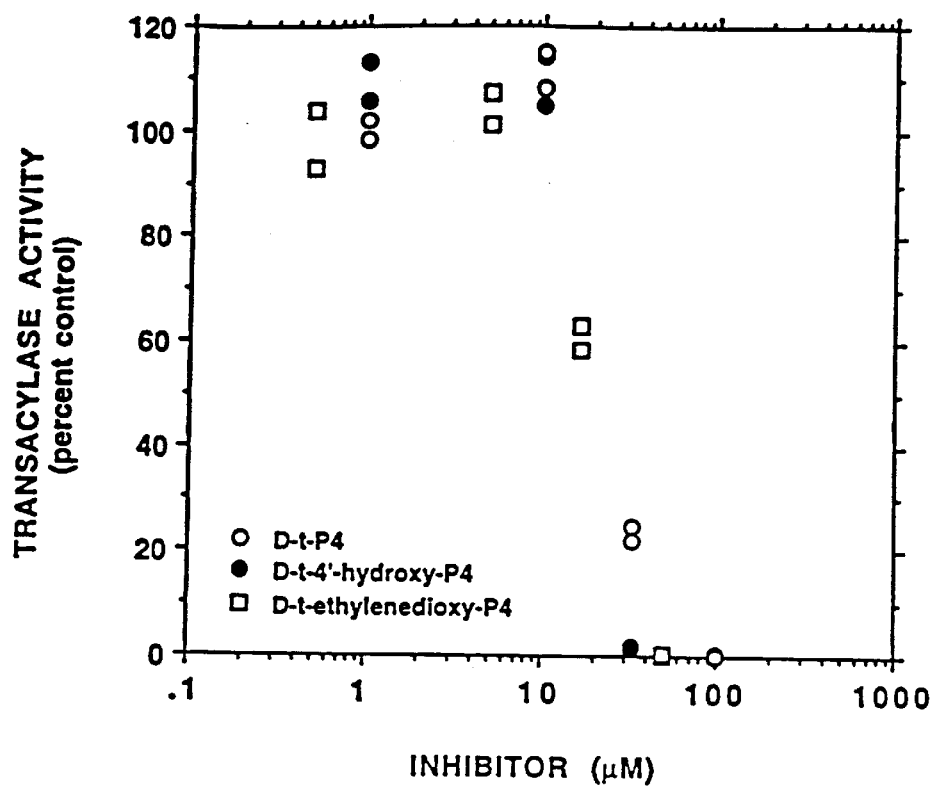
FIG. 12 is a graph showing the effects of D-threo enantiomers of P4, 4'-hydroxy-P4 and 3',4'-ethylenedioxy-P4 on 1-O-acyceramide synthase activity.

Distinguishing Between Inhibition of GlcCer Synthase and 1-O-acylceramide Synthase Inhibition Prior studies on PDMP and related homologues revealed that both the threo and erythro diastereomers were capable of increasing cell ceramide and inhibiting cell growth in spite of the observation that only the D-threo enantiomers blocked GlcCer synthase. An alternative pathway for ceramide metabolism was subsequently identified, the acylation of ceramide at the 1-hydroxyl position, which was blocked by both threo and erythro diastereomers of PDMP. The specificities of D-threo-P4, D-threo-3',4'-ethylenedioxy-P4, and D-threo-(4'-hydroxy)-P4 for GlcCer synthase were studied by assaying the transacylase. Although there was an ca. 100 fold difference in activity between D-threo-3',4'-ethylenedioxy-P4, D-threo-(4'-hydroxy)-P4, and D-threo-P4 ($IC_{50}$ 0.1 mM versus 10 mM) in inhibiting GlcCer synthase, the D-threo enantiomers of all three compounds demonstrated comparable activity in blocking 1-O-acylceramide synthase (FIG. 12).

In order to determine whether inhibition of 1-O-acylceramide synthase was the basis for inhibitor mediated ceramide accumulation, the ceramide and diradylglycerol levels of MDCK cells treated D-threo-P4, D-threo-3',4'-ethylenedioxy-P4, and D-threo-(4'-hydroxy)-P4 were measured (Table 9). MDCK cells ($5 \times 10^5$) were seeded into a 10 cm dish and incubated for 24 h. Following the incubation, the cells were treated for 24 or 48 h with or without P4 or the phenyl substitute homologues. Both ceramide and diradylglycerol contents were determined by the method of Preis, J. et al., *J. Biol. Chem.* 261:8597–8600 (1986). GlcCer content was measured densitometrically by a video camera and use of NIH image 1.49. Significant increases in both ceramide and diradylglycerol occurred only in cells treated with inhibitor concentrations in excess of 1 mM. This was approximately 30-fold lower than the concentration required for inhibition of the 1-O-acylceramide synthase assayed in the cellular homogenates. This disparity in concentration effects most likely reflects the ability of the more potent homologues to accumulate within intact cells. Abe, A. et al., *Biochim. Biophys. Acta* 1299:331–341 (1996).

TABLE 9

GlcCer, ceramide and diradylglycerol content of MDCK cells treated with D-threo-P4, D-threo-3',4'-ethylenedioxy-P4, and D-threo-(4'-hydroxy)-P4

| Condition | Ceramide (pmol/nmol phospholipid) | Diradylglycerol (pmol/nmol phospholipid) |
|---|---|---|
| Control | | |
| 24 h | 4.53 ± 0.12 | 24.2 ± 2.36 |
| 48 h | 6.68 ± 0.49 | 32.3 ± 3.11 |
| D-threo-P4 | | |
| 11.3 nM | | |
| 24 h | 5.33 ± 0.41* | 24.1 ± 1.66 |
| 48 h | 5.68 ± 0.27* | 29.6 ± 0.73 |

TABLE 9-continued

GlcCer, ceramide and diradylglycerol content of MDCK cells treated with D-threo-P4, D-threo-3',4'-ethylenedioxy-P4, and D-threo-(4'-hydroxy)-P4

| Condition | Ceramide (pmol/nmol phospholipid) | Diradylglycerol (pmol/nmol phospholipid) |
|---|---|---|
| 113 nM | | |
| 24 h | 4.64 ± 0.38 | 26.6 ± 1.56 |
| 48 h | 7.08 ± 0.29 | 33.0 ± 2.63 |
| 1130 nM | | |
| 24 h | 5.10 ± 0.35 | 27.1 ± 0.67 |
| 48 h | 9.74 ± 0.53* | 38.8 ± 1.11 |
| D-threo-4'-hydroxy-P4 | | |
| 11.3 nM | | |
| 24 h | 4.29 ± 0.71 | 30.9 ± 2.01* |
| 48 h | 6.70 ± 0.29 | 38.4 ± 1.44* |
| 113 nM | | |
| 24 h | 5.09 ± 0.95 | 31.5 ± 3.84* |
| 48 h | 7.47 ± 0.29 | 41.5 ± 0.66* |
| 1130 nM | | |
| 24 h | 7.38 ± 0.13 | 38.5 ± 3.84* |
| 48 h | 13.4 ± 1.03* | 47.2 ± 2.51* |
| D-threo-3',4'-ethylenedioxy-P4 | | |
| 11.3 nM | | |
| 24 h | 5.24 | 22.0 |
| | 5.04 | 24.7 |
| 113 nM | | |
| 24 h | 5.21 | 32.5 |
| | 5.21 | 41.6 |
| 1130 nM | | |
| 24 h | 9.64 | 32.5 |
| | 13.0 | 41.6 |

*Denotes $p < 0.05$ by the Student t test. For the D-threo-(ethylenedioxy)-P4 only two determinations were made.

Figure 7:
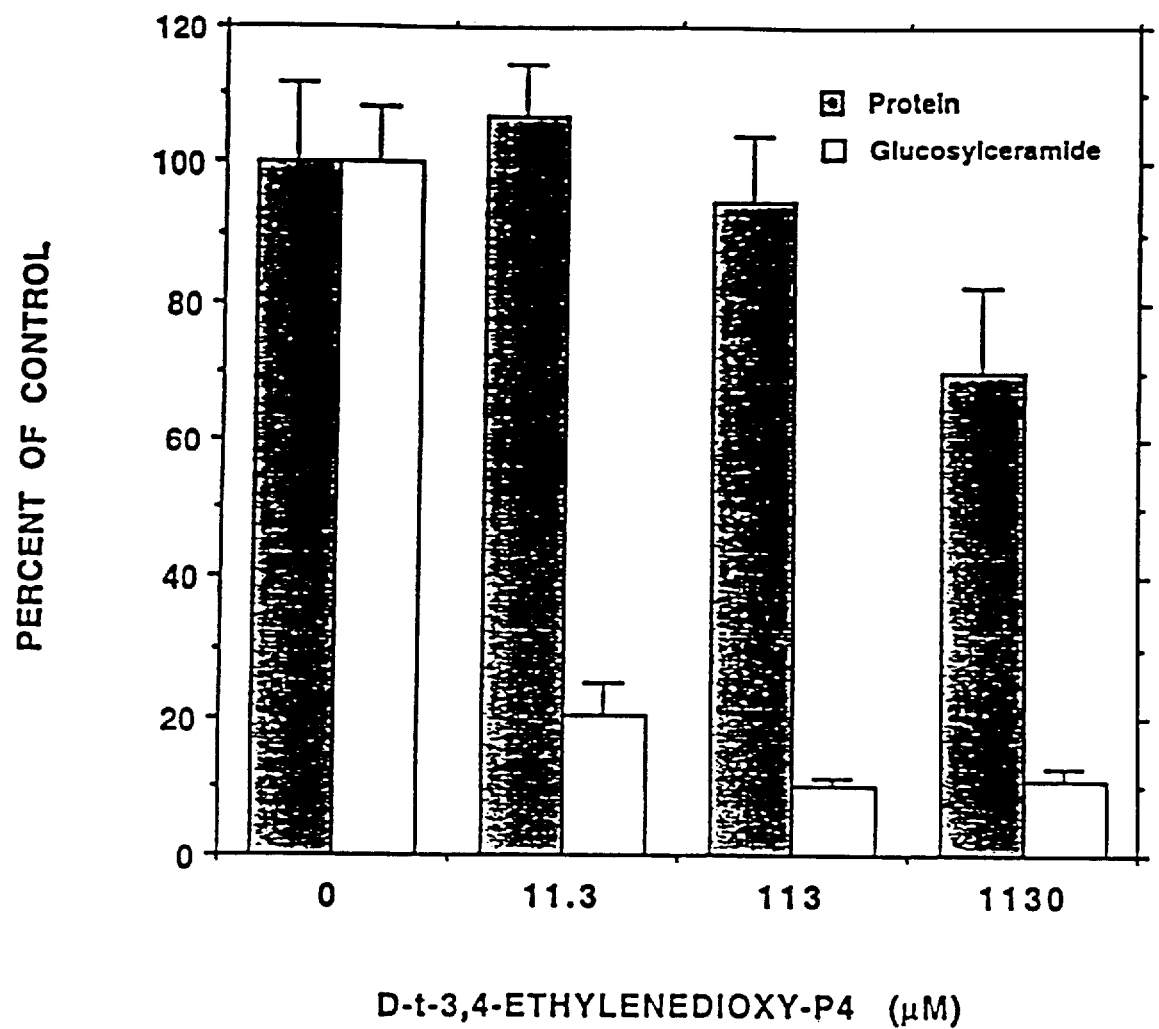
FIG. 7 is a bar graph showing the effects of D-t-3',4'-ethylenedioxy-P4 on GlcCer synthesis and cell growth.

Effects of D-threo-P4, D-threo-4'-hydroxy-P4 and D-threo-3,4'-ethylenedioxy-P4 on GlcCer Synthesis and Cell Growth To confirm the cellular specificity of D-threo-3',4'-ethylenedioxy-P4 and D-threo-(4'-hydroxy)-P4 as compared to D-threo-P4, MDCK cells were treated with different concentrations of the inhibitors. The total protein amount in each sample was determined by the BCA method. In GlcCer analysis, lipid samples and standard lipids were applied to the same HPTLC plate pre-treated with borate and developed in a solvent consisting of C/M/W (63/24/4). The level of GlcCer was estimated from a standard curve obtained using a computerized image scanner. The values were normalized on the basis of the phospholipid content. The results are shown in FIG. 7, wherein each bar is the average values from three dishes, with error bars corresponding to one standard deviation. In the control, the total protein and GlcCer were 414±47.4 μg/dish and 24.3±1.97 ng/nmol phosphate, respectively.

Figure 13:
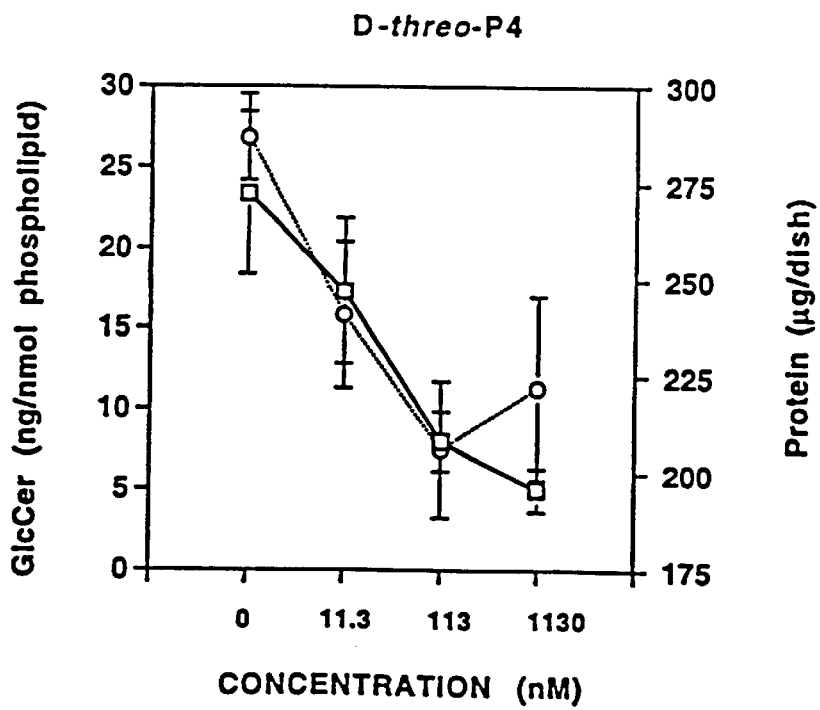
FIG. 13 is a graph showing the effect of D-threo-P4 on GlcCer synthesis and cell growth.
Figure 14:
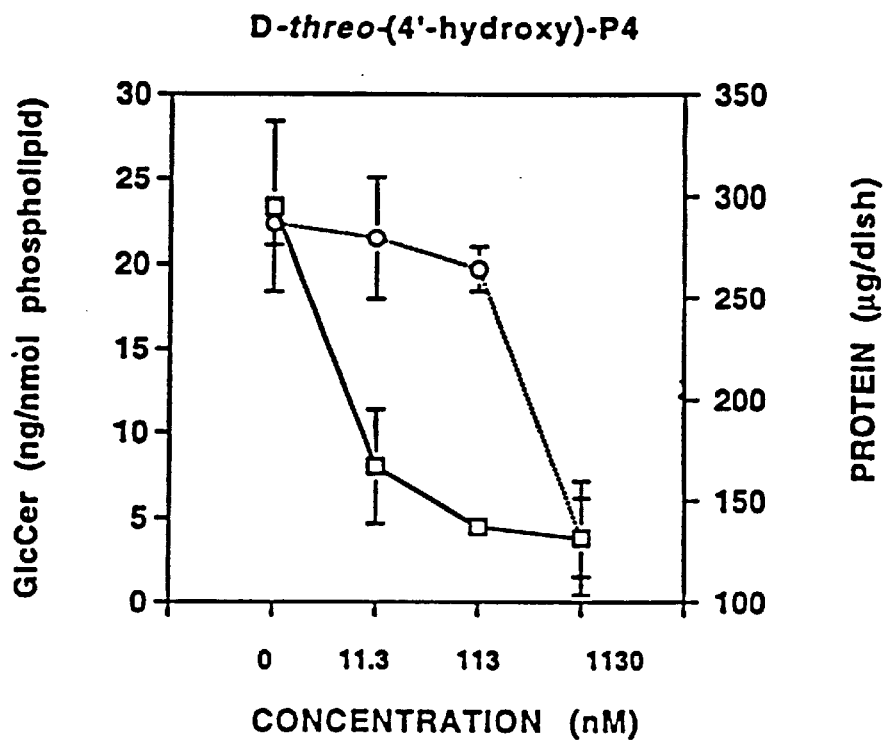
FIG. 14 is a graph showing the effect of D-threo-4'-hydroxy-P4 on GlcCer synthesis and cell growth.
Figure 15:
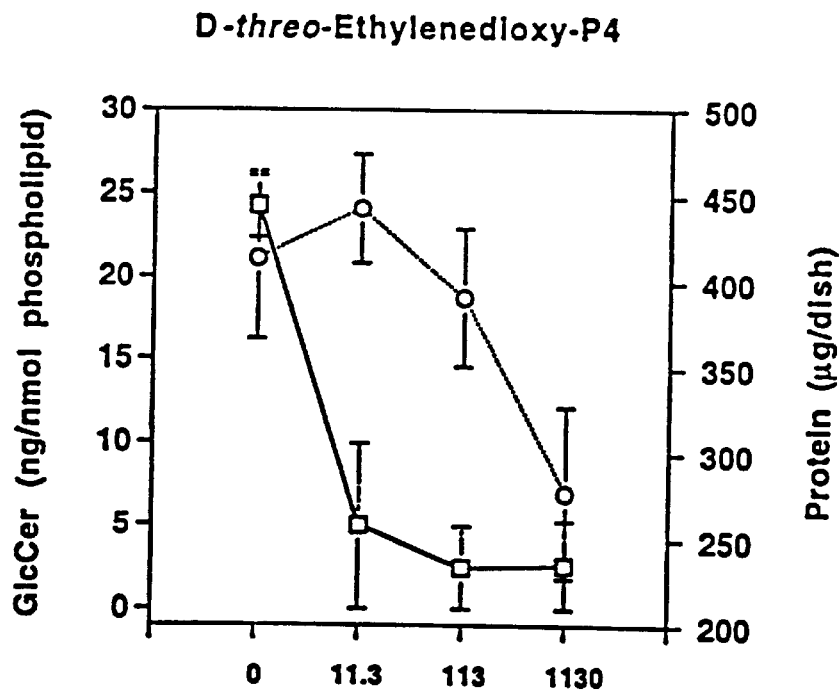
FIG. 15 is a graph showing the effect of D-threo-3',4'-ethylenedioxy-P4 on GlcCer synthesis and cell growth.

Approximately 66 and 78% of the GlcCer was lost from the cells treated by 11.3 nM D-threo-4'-hydroxy-P4 and D-threo-3',4'-ethylenedioxy-P4 respectively (FIGS. 7, 14 and 15). By contrast, only 27 percent depletion of GlcCer occurred in cells exposed to D-threo-P4 (FIG. 13). A low level of GlcCer persisted in the cells treated with 113 or 1130 nM of either compound. This may be due to the contribution, by degradation, of more highly glycosylated sphingolipids or the existence of another GlcCer synthase that is insensitive to the inhibitor.

On the other hand, there was little difference in the total protein content between untreated and treated cells with 11.3 or 113 nM nM D-threo-4'-hydroxy-P4 and D-threo-3',4'-ethylenedioxy-P4 (FIGS. 14 and 15). A significant decrease in total protein was observed in the cells treated with 1130 nM of either P4 homologue. In addition, the level of ceramide in the cells treated with 1130 nM D-threo-3',4'-ethylenedioxy-P4 and D-threo-(4'-hydroxy)-P4 was two times higher than that measured in the untreated cells (Table 9). There was no change in ceramide or diradylglycerol levels in cells treated with 11.3 nM or 113 nM concentrations of either compound. Similar patterns for GlcCer levels and protein content were observed at 48 h incubations.

The phospholipid content was unaffected at the lower concentrations of either D-threo-3',4'-ethylenedioxy-P4 or D-threo-(4'-hydroxy)-P4. The ratios of cell protein to cellular phospholipid phosphate (mg protein/nmol phosphate) were 4.94±0.30, 5.05±0.21, 4.84±0.90, and 3.97±0.29 for 0, 11.3, 113, and 1130 nM D-threo-3',4'-ethylenedioxy-P4 respectively, and 4.52±0.39, 4.35±0.10, and 3.68±0.99 for 11.3, 113, and 1130 nM D-threo-4'-hydroxy-P4 suggesting that the changes in GlcCer content were truly related to inhibition of GlcCer synthase activity. These results strongly indicate that the inhibitors D-threo-4'-hydroxy-P4 and D-threo-3',4'-ethylenedioxy-P4, are able to potently and specifically inhibit GlcCer synthesis in intact cells at low nanomolar concentrations without any inhibition of cell growth.

SPECIFIC EXAMPLE 3

Compositions within the scope of invention include those comprising a compound of the present invention in an effective amount to achieve an intended purpose. Determination of an effective amount and intended purpose is within the skill of the art. Preferred dosages are dependent for example, on the severity of the disease and the individual patient's response to the treatment.

As used herein, the term "pharmaceutically acceptable salts" is intended to mean salts of the compounds of the present invention with pharmaceutically acceptable acids, e.g., inorganic acids such as sulfuric, hydrochloric, phosphoric, etc. or organic acids such as acetic.

Pharmaceutically acceptable compositions of the present invention may also include suitable carriers comprising excipients and auxiliaries which facilitate processing of the active compounds into preparations which may be used pharmaceutically. Such preparations can be administered orally (e.g., tablets, dragees and capsules), rectally (e.g., suppositories), as well as administration by injection.

The pharmaceutical preparations of the present invention are manufactured in a manner which is itself known, e.g., using the conventional mixing, granulating, dragee-making, dissolving or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, e.g., lactose or sucrose, mannitol or sorbitol, cellulose preparations and/or calcium phosphates, e.g., tricalcium diphosphate or calcium hydrogen phosphate, as well as binders such as starch paste, using, e.g., maize starch, wheat starch, rice starch, potato starch, gelatin, gum tragacanth, methyl cellulose and/or polyvinylpyrrolidone. If desired, disintegrating agents may be added such as the above-mentioned starches and also carboxymethyl starch, cross-linked polyvinylpyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvent or solvent mixtures. In order to produce coatings resistant to gastric juices, solutions of suitable cellulose preparations, such as acetylcellulose phthalate or hydroxypropylmethyl cellulose phthalate, are used. Dyestuffs or pigments may be added to the tablets or dragee coatings, e.g., for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be used.

Possible pharmaceutical preparations which can be used rectally include, e.g., suppositories, which consist of a combination of the active compounds with a suppository base. Suitable suppository bases are, e.g., natural or synthetic triglycerides, paraffin hydrocarbons, polyethylene glycols or higher alkanols. It is also possible to use gelatin rectal capsules which consist of a combination of the active compounds with a base. Possible base materials include, e.g., liquid triglycerides, polyethylene glycols or paraffin hydrocarbons.

Suitable formulations for parenteral administration include aqueous solutions of the active compounds in water-soluble form, e.g., water-soluble salts. In addition, suspension of the active compounds as appropriate oily injection suspensions may be administered. Suitable lipophilic solvents or vehicles include fatty oils, such as sesame oil, or synthetic fatty acid esters, e.g., ethyl oleate or triglycerides. Aqueous injection suspensions may contain substances which increase the viscosity of the suspension such as sodium carboxymethylcellulose, sorbitol and/or dextran. Optionally, the suspension may also contain stabilizers.

Alternatively, the active compounds of the present invention may be administered in the form of liposomes, pharmaceutical compositions wherein the active compound is contained either dispersed or variously present in corpuscles consisting of aqueous concentrate layers adherent to hydrophobic lipidic layer. The active compound may be present both in the aqueous layer and in the lipidic layer or in the non-homogeneous system generally known as a lipophilic suspension.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All publications cited herein are expressly incorporated by reference.

We claim:

1. A compound wherein the compound is D-t-3',4'-ethylenedioxy-1-phenyl-2-palmitoylamino-3-pyrrolidino-1-propanol or pharmaceutically acceptable salts thereof.

2. A compound wherein the compound is D-t-4'-hydroxy-1-phenyl-2-palmitoylamino-3-pyrrolidino-1-propanol or pharmaceutically acceptable salts thereof.

3. A composition comprising a carrier and a compound selected from the group consisting of D-t-3',4'-ethylenedioxy-1-phenyl-2-palmitoylamino-3-pyrrolidino-1-propanol, D-t-4'-hydroxy-1-phenyl-2-palmitoylamino-3-pyrrolidino-1-propanol, pharmaceutically acceptable salts thereof and mixtures thereof.

4. The composition of claim 3, wherein the compound is D-t-3',4'-ethylenedioxy-1-phenyl-2-palmitoylamino-3-pyrrolidino-1-propanol.

5. The composition of claim 3, wherein the compound is a pharmaceutically acceptable salt of D-t-3',4'-ethylenedioxy-1-phenyl-2-palmitoylamino-3-pyrrolidino-1-propanol.

6. The composition of claim 3, wherein the compound is D-t-4'-hydroxy-1-phenyl-2-palmitoylamino-3-pyrrolidino-1-propanol.

7. The composition of claim 3, wherein the compound is a pharmaceutically acceptable salt of D-t-4'-hydroxy-1-phenyl-2-palmitoylamino-3-pyrrolidino-1-propanol.

8. A method for treating a patient having sphingolipidosis by reducing glycosphingolipid synthesis comprising the step of administering to the patient a therapeutically effective amount of a compound selected from the group consisting of D-t-3',4'-ethylenedioxy-1-phenyl-2-palmitoylamino-3-pyrrolidino-1-propanol, D-t-4'-hydroxy-1-phenyl-2-palmitoylamino-3-pyrrolidino-1-propanol, pharmaceutically acceptable salts thereof and mixtures thereof.

9. The method of claim 8, wherein the patient is diagnosed as having Gaucher disease.

10. The method of claim 8, wherein the patient is diagnosed as having Tay-Sachs disease.

11. The method of claim 8, wherein the patient is diagnosed as having Fabry disease.

* * * * *